US008961981B2

(12) United States Patent
Kaminski et al.

(10) Patent No.: US 8,961,981 B2
(45) Date of Patent: Feb. 24, 2015

(54) TARGETING THE NEUROMUSCULAR JUNCTION FOR TREATMENT

(75) Inventors: Henry Kaminski, Washington, DC (US); Linda Kusner, Washington, DC (US); Namita Satija, St. Louis, MO (US)

(73) Assignee: Saint Louis University, St. Louis, MO (US)

(*) Notice: Subject to any disclaimer, the term of this patent is extended or adjusted under 35 U.S.C. 154(b) by 152 days.

(21) Appl. No.: 13/527,142

(22) Filed: Jun. 19, 2012

(65) Prior Publication Data

US 2012/0321624 A1 Dec. 20, 2012

Related U.S. Application Data

(60) Provisional application No. 61/498,707, filed on Jun. 20, 2011.

(51) Int. Cl.

| | |
|---|---|
| *A61K 47/48* | (2006.01) |
| *C07K 16/28* | (2006.01) |
| *C07K 16/18* | (2006.01) |
| *C07K 19/00* | (2006.01) |
| *C07K 14/46* | (2006.01) |
| *C07K 14/78* | (2006.01) |
| *C07K 14/705* | (2006.01) |
| *C07K 14/81* | (2006.01) |
| *C07K 14/435* | (2006.01) |
| *C07K 14/005* | (2006.01) |
| *A61K 39/00* | (2006.01) |
| *A61K 38/00* | (2006.01) |

(52) U.S. Cl.
CPC ..... *A61K 47/48246* (2013.01); *C07K 14/70596* (2013.01); *C07K 14/78* (2013.01); *C07K 14/811* (2013.01); *C07K 16/286* (2013.01); *C07K 14/43527* (2013.01); *C07K 14/46* (2013.01); *A61K 47/48561* (2013.01); *C07K 14/005* (2013.01); *A61K 2039/505* (2013.01); *C07K 2317/622* (2013.01); *C07K 2319/00* (2013.01); *C07K 2319/21* (2013.01); *C07K 2319/23* (2013.01); *C07K 2319/30* (2013.01); *C07K 2319/50* (2013.01); *A61K 38/00* (2013.01); *C12N 2740/16222* (2013.01); *C12N 2760/20122* (2013.01)
USPC ............... 424/178.1; 424/185.1; 424/192.1; 424/134.1; 424/135.1; 424/181.1; 424/193.1; 530/388.22; 530/317; 530/387.3; 530/300; 514/17.7; 514/21.4

(58) Field of Classification Search
None
See application file for complete search history.

(56) References Cited

U.S. PATENT DOCUMENTS

| | | | | |
|---|---|---|---|---|
| 5,196,193 | A * | 3/1993 | Carroll | 424/172.1 |
| 6,632,790 | B1 * | 10/2003 | Yurchenco | 514/21.2 |
| 7,884,188 | B2 | 2/2011 | Nunn | |
| 2003/0138432 | A1 * | 7/2003 | Glazier | 424/178.1 |
| 2003/0226155 | A1 | 12/2003 | Sadeghi et al. | |
| 2005/0107601 | A1 | 5/2005 | Loeb | |
| 2005/0266010 | A1 * | 12/2005 | Hott et al. | 424/178.1 |
| 2006/0013809 | A1 * | 1/2006 | Vincent et al. | 424/133.1 |
| 2009/0209459 | A1 | 8/2009 | Hamer et al. | |

FOREIGN PATENT DOCUMENTS

WO WO 2004/106369 * 12/2004

OTHER PUBLICATIONS

Colman et al., in Research in Immunology (145(1):33-36, 1994.*
Wu et al., J Mol Biol 294: 151-162, 1999.*
Yu et al., Investigative Ophthalmology & Visual Science 49(2): 522-527, Feb. 2008.*
Soltys et al., Ann Neurol 65: 67-75, Jan. 2009.*
Curtis et al., PNAS 88: 5809-5813; Jul. 1991.*
Lee et al., Immunology and Cell Biology 86: 153-160, 2008.*
Invitation to Pay Additional Fees and, Where Applicable, Protest Fee issued for PCT/US12/43172, dated Nov. 8, 2012, pp. 2.
Soltys et al, "Novel complement inhibitor limits severity of experimental myasthenia gravis," Ann Neurol., vol. 65, pp. 67-75 (2009).
Hillmen et al, "The complement inhibitor eculizumab in paroxysmal nocturnal hemoglobinuria," N Engl J Med., vol. 355, pp. 1233-1243 (2006).
Kusner et al, "Effect of complement and its regulation on myasthenia gravis pathogenesis," Expert Rev Clin Immunol., vol. 4, pp. 43-52 (2008).
Zhou et al, "Anti-c5 antibody treatment ameliorates weakness in experimentally acquired myasthenia gravis," J Immunol., vol. 179, pp. 8562-8567 (2007).
Lindstrom J., "Acetylcholine receptors and myasthenia," Muscle Nerve., vol. 23, pp. 453-477 (2000).
Christadoss et al, "Animal models of myasthenia gravis," Clin Immunol., vol. 94, pp. 75-87 (2000).
Sahashi et al, Ultrastructural localization of the terminal and lytic ninth complement component (C9) at the motor end-plate in myasthenia gravis, J Neuropathol Exp Neurol., vol. 39, pp. 160-172 (1980).
Nakano et al, "Myasthenia gravis: quantitative immunocytochemical analysis of inflammatory cells and detection of complement membrane attack complex at the end-plate in 30 patients," Neurology, vol. 43, pp. 1167-1172 (1993).
Lennon et al, "Role of complement in the pathogenesis of experimental autoimmune myasthenia gravis," J Exp Med., vol. 147, pp. 973-983 (1978).
Ruff et al, "End-plate voltage-gated sodium channels are lost in clinical and experimental myasthenia gravis," Ann Neurol., vol. 43, pp. 370-379 (1998).
Chamberlain-Banoub et al, "Complement membrane attack is required for endplate damage and clinical disease in passive experimental myasthenia gravis in Lewis rats," Clin Exp Immunol., vol. 146, pp. 278-286 (2006).
Christadoss P., "C5 gene influences the development of murine myasthenia gravis," J Immunol., vol. 140, pp. 2589-2592 (1988).
Biesecker et al, "Inhibition of acute passive transfer experimental autoimmune myasthenia gravis with Fab antibody to complement C6," J Immunol., vol. 142, pp. 2654-2659 (1989).

(Continued)

*Primary Examiner* — Phuong Huynh
(74) *Attorney, Agent, or Firm* — Stinson Leonard Street LLP

(57) ABSTRACT

Compositions and methods for targeting therapeutic agents to neuromuscular junctions are disclosed. Also disclosed are methods for treating diseases and conditions affecting the neuromuscular junction. Compositions include a neuromuscular junction targeting peptide coupled to a therapeutic agent. Compositions may further include a linker peptide. Methods for targeting therapeutic agents to neuromuscular junctions and treating diseases and conditions affecting the neuromuscular junction include administering a composition including a neuromuscular junction targeting peptide coupled to a therapeutic agent.

8 Claims, 14 Drawing Sheets

(56) References Cited

OTHER PUBLICATIONS

Piddlesden et al, "Soluble complement receptor 1 (sCR1) protects against experimental autoimmune myasthenia gravis," J Neuroimmunol., vol. 71, pp. 173-177 (1996).

Kaminski et al, "Deficiency of decay accelerating factor and CD59 leads to crisis in experimental myasthenia," Exp Neurol. vol. 202, pp. 287-293 (2006).

Lin et al, "Enhanced Susceptibility to Experimental Autoimmune Myasthenia Gravis in the Absence of Decay-Accelerating Factor Protection," J Clin Invest., vol. 110, pp. 1269-1274 (2002).

Morgan et al., "The membrane attack pathway of complement drives pathology in passively induced experimental autoimmune myasthenia gravis in mice," Clin Exp Immunol., vol. 146, pp. 294-302 (2006).

Tuzun et al, "Genetic evidence for involvement of classical complement pathway in induction of experimental autoimmune myasthenia gravis," J Immunol., vol. 171 pp. 3847-3854 (2003).

Engel et al., "Immune complexes (IgG and C3) at the motor end-plate in myasthenia gravis. Ultrastructure and light microscopic localization and electrophysiological correlations," Mayo Clin Proc., vol. 52, pp. 267-280 (1977).

Lindstrom et al, "Production and assays of antibodies to acetylcholine receptors," Methods Enzymol., vol. 74, pp. 432-456 (1981).

Halstead et al, "C5 inhibitor rEV576 protects against neural injury in an in vitro mouse model of Miller Fisher syndrome," J Peripher Nerv Syst., vol. 13, pp. 228-235 (2008).

Bracci et al., "Molecular mimicry between the rabies virus glycoprotein and human immunodeficiency virus-1 GP120: cross-reacting antibodies induced by rabies vaccination," Blood, Nov. 1, 1997, vol. 90, No. 9, pp. 3623-3628.

Qu et al., Recent developments in low molecular weight complement inhibitors, Molecular Immunology, vol. 47, dated 2009, pp. 185-195.

\* cited by examiner

FIG. 6

| ATG | His tag | Thrombin | RVG | linker | rEV |

FIG. 9

| KDa | M | 1 | 2 | 3 | 4 | 5 | 6 | |
|---|---|---|---|---|---|---|---|---|
| 116.0 | | | | | | | | |
| 66.2 | | | | | | | | ←scFv-DAF |
| 45.0 | | | | | | | | |
| 35.0 | | | | | | | | |
| 25.0 | | | | | | | | |
| 18.4 | | | | | | | | |
| 14.4 | | | | | | | | |

TARGETING THE NEUROMUSCULAR JUNCTION FOR TREATMENT

CROSS-REFERENCE TO RELATED APPLICATIONS

This application claims priority to provisional patent application No. 61/498,707, filed on Jun. 20, 2011, which is incorporated herein by reference in its entirety.

STATEMENT REGARDING FEDERALLY SPONSORED RESEARCH OR DEVELOPMENT

This invention was made with government support under Grant Award No. EY14837 awarded by the National Eye Institute of the National Institutes of Health. The government may have certain rights in the invention.

INCORPORATION OF SEQUENCE LISTING

A paper copy of the Sequence Listing and a computer readable form of the sequence containing the file named "31065-31_ST25.txt", which is 32,859 bytes in size (as measured in MICROSOFT WINDOWS® EXPLORER), are provided herein and are herein incorporated by reference. This Sequence Listing consists of SEQ ID NOs: 1-38.

BACKGROUND OF THE DISCLOSURE

The present disclosure relates generally to compositions and methods for targeting therapeutic agents. More particularly, the present disclosure relates to compositions and methods useful for targeting therapeutic agents to the neuromuscular junction using neuromuscular junction targeting peptides.

The neuromuscular junction is the point at which nerve signals the muscle to contract. More particularly, the neuromuscular junction is the synapse or junction of the axon terminal of a neuron with a muscle fiber plasma membrane.

Several diseases involve the neuromuscular junction as the primary site of injury. For example, myasthenia gravis is an autoimmune disorder that is caused by autoantibodies directed primarily toward the skeletal muscle acetylcholine receptor (AChR) at the neuromuscular junction. The antibodies bind to the post-synaptic surface of the neuromuscular junction and produce a reduction in AChR number and damage the muscle endplate, which leads to a failure of neuromuscular transmission that results in muscle weakness. Another category of gravis is caused by antibodies against muscle specific kinase ("MuSK") at the neuromuscular junction. Lambert-Eaton syndrome is yet another disorder characterized by the attack of voltage-gated calcium channels at the neuromuscular junction by antibodies. Miller Fischer syndrome is another disorder involving the attack of nerve terminals by antibodies.

The complement system may underlie one effector mechanism for antibody-mediated immunity, which begins with antibody binding to a cell surface antigen and the formation of a membrane attack complex. The membrane attack complex is a multimeric protein complex that produces cell lysis and, in the case of myasthenia gravis, destruction of the neuromuscular junction. In antibody-initiated activation of the complement cascade, nascent C4b and C3b fragments condense with free hydroxyl and amino groups on biological membranes. Once bound, these fragments serve as sites for assembly of C4b2a and C3bBb, the central amplification enzymes of the cascade. Control of their activities to protect host tissues from autologous complement-mediated injury is through a system of cell-associated and serum regulatory proteins.

Complement inhibitors are a class of drugs that show promise for treating neuromuscular diseases. Complement inhibitors may stop the body's immune response system from attacking itself. Eculizumab, for example, is an anti-C5 antibody that is approved for use in paroxysmal nocturnal hemoglobinuria and in Phase 2 trials as a treatment for myasthenia gravis. Eculizumab functions by inhibiting complement. Because administration occurs by infusion, the agent may inhibit complement throughout the body.

Another complement inhibitor is rEV576 (OmCI or Conversin). rEV576 is an 18.5 kDa recombinantly produced protein derived from tick (*Ornithodoros moubata*) saliva that specifically inhibits C5 complement. rEV576 appears to directly bind C5 to prevent interaction with C5 convertase. Administration of rEV576 has been shown to reduce serum complement activity, diminish C9 deposition at the neuromuscular junction, and reduce cytotoxicity of serum from treated animals.

Therapies for myasthenia gravis generally focus on enhancing neuromuscular transmission by inhibition of cholinesterase using agents such as pyridostigmine. Other treatments such as corticosteroids, azathioprine, tacrolimus, and mycophenolate, are directed to suppressing or modulating the immune system. Acute exacerbations of weakness may be treated by plasmapheresis or intravenous immunoglobulins. While effective, these treatments can be expensive and may entail side affects that affect organ systems beyond the neuromuscular junction. These treatments may additionally result in systemic side effects because administration occurs throughout the body. The immunotherapies are not specifically focused on myasthenia gravis, but rather generally moderate immune response through reduction of autoantibody levels directly or indirectly through suppression of B and T cell activity.

Although treatments are available for conditions resulting from neuromuscular junction injury, there remains a concern over their efficacy, side-effects, and/or costs. Moreover, complement inhibitor strategies rely on systemic inhibition of complement. Accordingly, there exists a continued need to develop alternative treatments and methods for treating conditions resulting from neuromuscular junction injury.

SUMMARY OF THE DISCLOSURE

The present disclosure relates generally to compositions and methods for targeting therapeutic agents. More particularly, the present disclosure relates to compositions and methods useful for targeting therapeutic agents to the neuromuscular junctions using neuromuscular junction targeting peptides.

In one aspect, the present disclosure is directed to compositions including a neuromuscular junction targeting peptide coupled to a therapeutic agent.

In another aspect, the present disclosure is directed to a method of delivering a therapeutic agent to a neuromuscular junction. The method includes administering a composition that includes a neuromuscular junction targeting peptide coupled to a therapeutic agent.

In another aspect, the present disclosure is directed to methods for treating a neuromuscular junction-related disease or condition. The method includes administering to a subject in need thereof a composition that includes a neuromuscular junction targeting peptide coupled to a therapeutic agent.

In another aspect, the present disclosure is directed to a recombinant nucleic acid construct encoding a neuromuscular junction targeting peptide operably linked to a heterologous nucleic acid sequence encoding a therapeutic polypeptide.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 6 is a schematic showing the domain structure of the RVG-rEV polypeptide as described in Example 3.

FIG. 9 is an SDS-gel showing the expression and purification of scFv-DAF as described in Example 4.

Figure 1:
FIG. 1 is a schematic showing the domain structure of the laminin-rEV polypeptide as described in Example 1.
Figure 2:
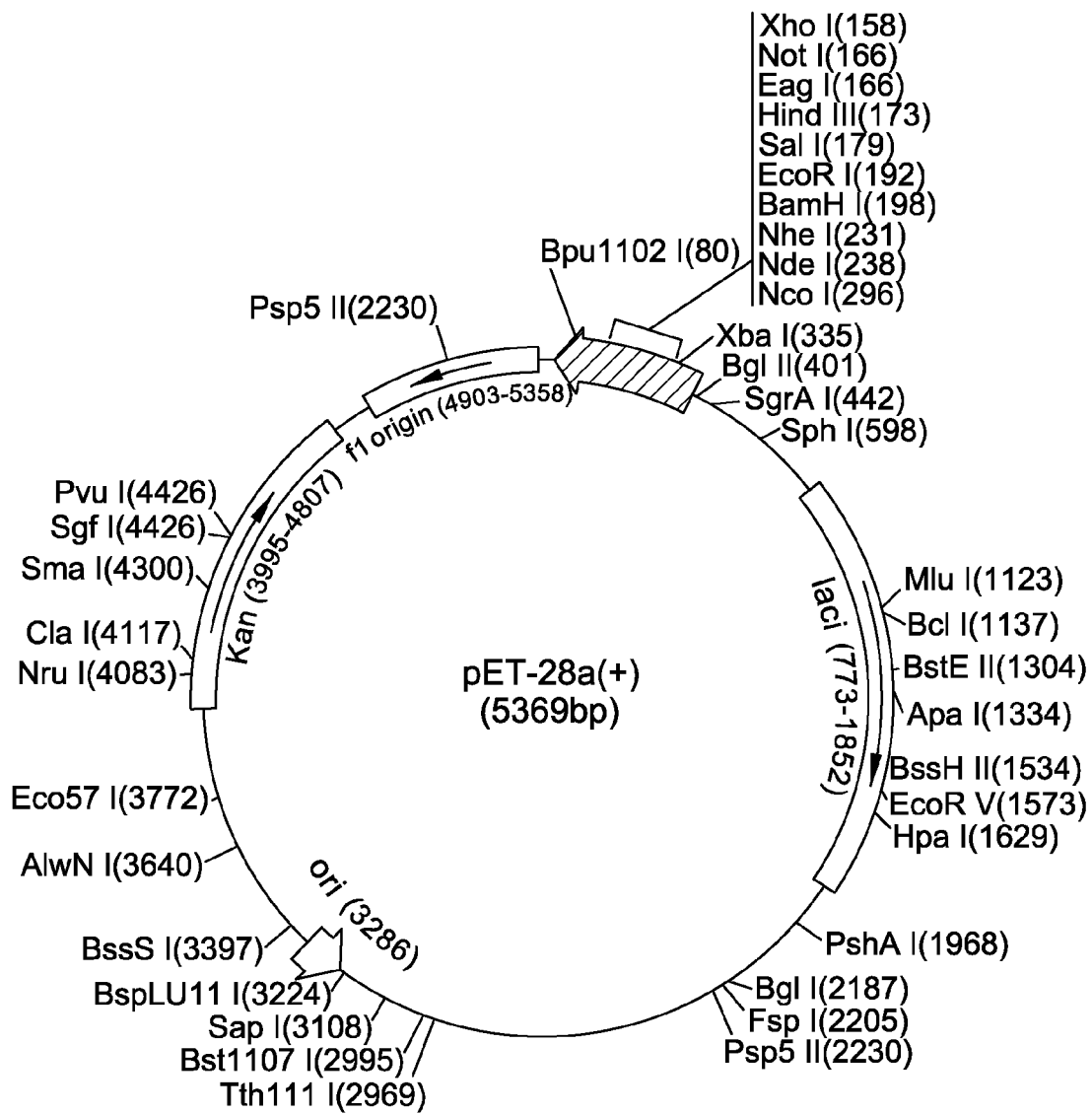
FIG. 2 is a map of the pET28a expression vector.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, compositions and methods have been discovered that allow for targeting neuromuscular junctions. The compositions and methods have significant impact as they allow for the targeted delivery of therapeutic agents to the neuromuscular junction. The compositions and methods further allow for the treatment of neuromuscular junction-related diseases and conditions such as, for example, myasthenia gravis, experimentally acquired myasthenia gravis, Lambert-Eaton syndrome, and Miller Fischer syndrome in which neuromuscular junctions may be affected.

Compositions

Figure 14:
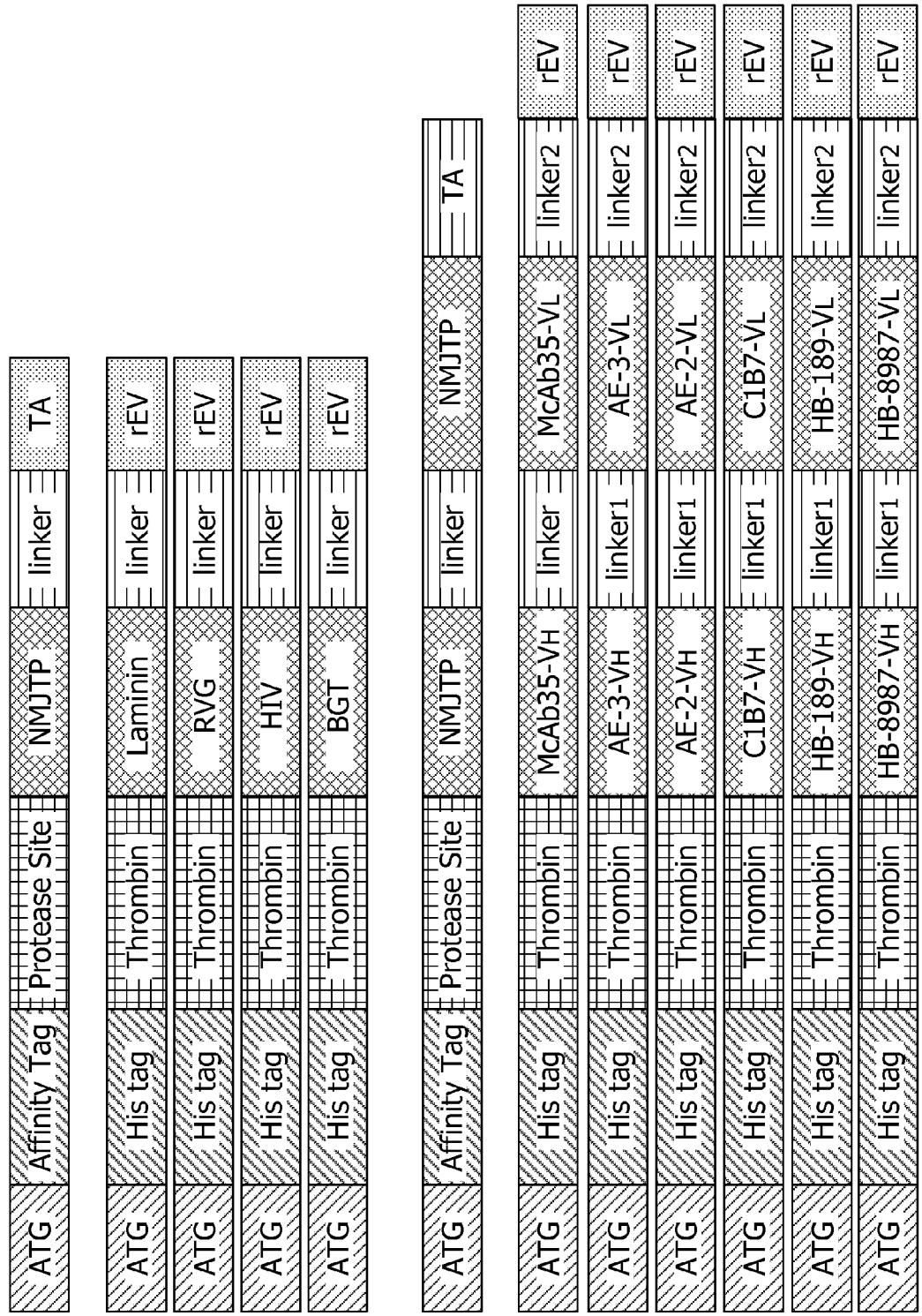
FIG. 14 is a schematic showing the domain structures of various neuromuscular junction targeting constructs according to the present disclosure.

In one aspect, the present disclosure is directed to a composition including a neuromuscular junction targeting peptide ("NMJTP") coupled to a therapeutic agent ("TA") (see e.g., FIG. 14). The terms "polypeptide," "peptide" and "protein" are used interchangeably herein to refer to a polymer of amino acid residues of any length, unless indicated otherwise.

As used herein, "coupled to" refers to a composition wherein the neuromuscular junction targeting peptide is directly or indirectly attached to, fused with, joined to, and/or linked to the therapeutic agent. For example, if the composition is prepared using known recombinant protein expression methods, a nucleic acid sequence encoding the neuromuscular junction targeting peptide may be joined to a nucleic acid sequence encoding the therapeutic agent. In such an example, the neuromuscular junction targeting peptide would be directly coupled to the therapeutic agent. In another example, the nucleic acid sequence encoding the neuromuscular junction targeting peptide may be indirectly joined to a nucleic acid sequence encoding the therapeutic agent by including at least one linker between the neuromuscular junction targeting peptide and the therapeutic agent.

The compositions of the present disclosure may be prepared as part of a larger construct that is subjected to further processing to produce the final composition having the neuromuscular junction targeting peptide coupled to the therapeutic agent. Domain structures of larger constructs are illustrated in FIG. 14. In one embodiment, for example, the construct may include an ATG start site coupled to an affinity tag coupled to a protease cleavage site ("Protease Site") coupled to a neuromuscular junction targeting peptide ("NMJTP") coupled to a linker coupled to a therapeutic agent ("TA") (see, FIG. 14). In another embodiment, the domain structure may include an ATG start site coupled to an affinity tag coupled to a protease cleavage site coupled to a NMJTP coupled to a linker coupled to a NMJTP coupled to a linker coupled to a TA (see, FIG. 14). Table 1 summarizes the neuromuscular junction targeting peptide indicated in FIG. 14 and their specificities (binding target).

TABLE 1

Neuromuscular Junction Targeting Peptides.

| NMJTP | Specificity |
| --- | --- |
| McAb35 | Muscle nicotinic acetylcholine receptor |
| AE-2 | Acetylcholinesterase |
| AE-3 | Acetylcholinesterase |
| C1B7 | Acetylcholinesterase |
| HB-189 | Neuronal acetylcholine receptor |
| HB8987 | Neuronal acetylcholine receptor alpha subunit |

The therapeutic agent may be coupled to either the N-terminus or C-terminus of the neuromuscular junction targeting peptide. After further processing as further described herein, for example, the composition may have the structure NMJTP-TA, in which the therapeutic agent is coupled to the C-terminus of the neuromuscular junction targeting peptide. In another example, the composition may have the structure TA-NMJTP after further processing, in which the therapeutic agent is coupled to the N-terminus of the neuromuscular junction targeting peptide. Similarly, the neuromuscular junction targeting peptide may be coupled to a linker at either the N-terminus, the C-terminus, or both the N-terminus and C-terminus of the neuromuscular junction targeting peptide (see, FIG. 14). When a linker is included in the composition, the linker is positioned between the neuromuscular junction targeting peptide and the therapeutic agent. In one embodiment, the composition may have the structure: NMJTP-linker-TA after further processing. In another embodiment, the composition may have the structure: TA-linker-NMJTP after further processing. In yet another embodiment, the composition may have the structure: NMJTP-linker-NMJTP-linker-TA after further processing. In still another embodiment, the composition may have the structure: TA-linker-NMJTP-linker-NMJTP after further processing.

As described herein, the composition may be subjected to further processing. For example, the presence of an affinity tag allows for purification via interaction between the affinity tag and an affinity substrate as known by those skilled in the art and described herein. The composition may also be subjected to treatment with a protease that cleaves the composition at a position between the affinity tag and the neuromuscular junction targeting peptide. Protease treatment allows for the preparation of a composition including a neuromuscular junction targeting peptide and a therapeutic agent, which may further include at least one linker.

Neuromuscular Junction Targeting Peptides

The composition of the present disclosure includes a neuromuscular junction targeting peptide ("NMJTP"). The neuromuscular junction targeting peptide may be a peptide molecule that binds to or interacts with a molecule located at or near the neuromuscular junction. For example, the molecule may be located at the presynaptic or postsynaptic side of the neuromuscular junction. Suitable neuromuscular junction targeting peptides may bind to or interact with a molecule present on a neuron at or near the neuromuscular junction. Other suitable neuromuscular junction targeting peptides may bind to or interact with a molecule present on a muscle cell at or near the neuromuscular junction. The neuromuscular junction targeting peptides have a binding affinity from about 0.5 nM to about 50 μM. A particularly suitable binding affinity may be, for example, from about 1 nM to about 40 μM. A even more suitable binding affinity may be, for example, from about 0.1 μM to about 0.75 μM. Binding of a neuromuscular targeting peptide may be determined by methods known by those skilled in the art. Suitable methods for determining binding affinity may be, for example, enzyme-linked immunosorbent assay (ELISA), Western blot analysis, and immunostaining. Neuromuscular junction targeting peptides alone or coupled to therapeutic agents may also be prepared using, for example, recombinant protein expression methods to further include a detectable label such as, for example, a fluorescent tag, such that binding may be directly detected. Analysis of immunostained or directly labeled compositions may be further analyzed by fluorescent pixel analysis, for example, to determine binding affinity.

Suitable neuromuscular junction targeting peptides may be, for example, peptides obtained from larger protein molecules. Other suitable neuromuscular junction targeting peptides may be, for example, antibody molecules. Particularly suitable antibody molecules may be, for example, antibody variable regions, antibody heavy chains, antibody light chains, Fab, $F(ab')_2$, F(ab') and single chain antibodies (scFv).

Suitable neuromuscular junction targeting peptides may be obtained from proteins such as, for example, laminin, a zinc finger domain of the human immunodeficiency virus (HIV) nucleocapsid protein, rabies virus glycoprotein (RVG), α-bungarotoxin, agrin, antibodies to the acetylcholine receptor, antibodies to acetylcholinesterase, muscle specific kinase, calcium channels, and sodium channels. Particularly suitable neuromuscular junction targeting peptides may be, for example, a laminin peptide, a human immunodeficiency virus peptide such as, for example, a zinc finger domain of the HIV nucleocapsid protein, a rabies virus glycoprotein peptide, an α-bungarotoxin peptide, an agrin peptide, a single chain antibody peptide that specifically binds to acetylcholinesterase and a single chain antibody peptide that specifically binds to acetylcholine receptor. Suitable neuromuscular junction targeting peptides may also be non-peptide chemicals, such as nicotine. Particularly suitable neuromuscular junction targeting peptides may be, for example, those having an amino acid sequence of SEQ ID NO: 2, SEQ ID NO: 4, SEQ ID NO: 6, SEQ ID NO: 7, SEQ ID NO: 8, and SEQ ID NO: 9.

Therapeutic Agents

The composition of the present disclosure includes a therapeutic agent that is coupled to the neuromuscular junction targeting peptide. As used herein, the term "therapeutic agent" refers to any type of drug, medicine, pharmaceutical, hormone, antibiotic, protein, gene, growth factor, bioactive material, etc., used for treating, controlling, or preventing diseases or medical conditions. As used herein, the term "derivative" refers to a compound or peptide obtained from another compound (e.g., a lead or parent compound). The therapeutic agent may be a protein that may be recombinantly expressed such that a nucleic acid sequence encoding an amino acid sequence corresponding to a therapeutic polypeptide may be operably linked to a nucleic acid sequence encoding an amino acid sequence corresponding to a neuromuscular junction targeting peptide and/or a nucleic acid sequence encoding an amino acid sequence corresponding to a linker.

Suitable therapeutic agents may be, for example, complement inhibitors, acetylcholinesterase inhibitors, trophic agents, and paralytic agents. Suitable complement inhibitors may be, for example, decay accelerating factor ("DAF"; "CD55")), rEV576, complement receptor 1 ("CR1"; "CD35"), membrane cofactor protein ("MCP"; "CD46"), compstatin, compstatin derivatives, POT-4, C1 inhibitor, C4b-binding protein ("C4BP"), factor H ("FH"), complement receptor Ig ("CRIg"), CD59 (complement regulatory protein), clusterin, C3-inhibitors, peptide 2J (CEGPFGPRHDLTFCW; SEQ ID NO:36), human beta-defensin 2, CRIT-H17 (C2 receptor inhibitor trispanning-H17), Ac-SHLGLAR-H (SEQ ID NO: 37), Ac-RLLLAR-H (SEQ ID NO: 38), C1s-INH-248 (synthetic small molecule inhibitor of C1s), S-protein, and Crry (complement receptor related protein). Other suitable therapeutic agents may be, for example, peptides obtained from full length complement inhibitors. For example, control protein repeats of DAF may be used as the therapeutic agent. Other suitable therapeutic agents such as chemicals and peptidomimetics, that are not peptides, but inhibit complement may be, for example, circumin, W-54011 (N-((4-Dimethylaminophenyl)methyl)-N-(4-isopropylphenyl)-7-methoxy-1,2,3,4-tetrahydronaphthalen-1-carboxamide), NGD 2000-1, NDT9520492 ((2S)—N-

(2,3-dihydro-1H-inden-2-yl)-N-[(2-fluorophenyl)methyl]-2-[(1R)-1-naphthalen-1-yl-3,4-dihydro-1H-isoquinolin-2-yl]propanamide), CP-447697 (4-{(1-Benzothiophen-3-ylcarbonyl)[2-(4-chlorophenyl)ethyl]amino}-N-(2,4-difluorophenyl)-1-piperidinecarboxamide), NDT 9513727 ([N,N-bis(1,3-benzodioxol-5-ylmethyl)-1-butyl-2,4-diphenyl-1H-imidazole-5-methanamine]), SB290157 ($N^2$-[(2,2-Diphenylethoxy)acetyl]-L-arginine), SB290157(A) (arginine-substituted SB290157), SB290157(B) (aminopiperidine-derivative SB290157), BCX1470 (2-amidino-6-[2-thiophene carboxy]benzothiophene methanesulfonate), a C1s inhibitor, PMX53 ((2S)-2-acetamido-N-[(3S,9S,12S,15R,18S)-15-(cyclohexylmethyl)-9-[3-(diaminomethylideneamino)propyl]-12-(1H-indol-3-ylmethyl)-2,8,11,14,17-pentaoxo-1,7,10,13,16-pentazabicyclo[16.3.0]henicosan-3-yl]-3-phenylpropanamide), PMX205 (hydrocinnamic acid substituted derivative of PMX53), C089 (NMe-Phe-Lys-Pro-D-Cha-Trp-D-Arg-COOH), and JPE1375 (hydroorotic acid-Phe-Orn-Pro-(d-HomoLeu)-(4-Fluoro-Phe)-Phe).

Particularly suitable therapeutic agents may be, for example, those having an amino acid sequence of SEQ ID NO: 11 and SEQ ID NO: 12.

Linkers

Additionally or alternatively, the composition may include at least one linker such that the neuromuscular junction targeting peptide is indirectly coupled to the therapeutic agent (see, FIG. 14). In one embodiment, the composition may include a linker positioned between the neuromuscular junction targeting peptide ("NMJTP") and the therapeutic agent ("TA") (see, FIG. 14). In another embodiment, the composition may include a linker positioned between two domains of the neuromuscular junction targeting peptide such as, for example, when the composition uses a single chain antibody wherein the first linker is positioned between a $V_H$ and a $V_L$ of the single chain antibody (see, FIG. 14). In embodiments using a single chain antibody as the neuromuscular junction targeting peptide, the two variable regions of the antibody are separated by a linker to allow proper folding so binding to the targeted protein may occur. For example, if the composition is prepared using known recombinant protein expression methods, a nucleic acid sequence encoding the neuromuscular junction targeting peptide may be coupled to a nucleic acid sequence encoding the linker that may be coupled to a nucleic acid sequence encoding the therapeutic agent.

Without intending to be bound by theory, it is believed that a linker provides additional distance or separation between the neuromuscular targeting peptide and the therapeutic agent, or also, for example, to limit possible steric hindrance that may otherwise interfere with the activity of the therapeutic agent or targeting by the neuromuscular junction targeting peptide. Linkers may further allow for may further allow for proper folding of the neuromuscular junction targeting peptides and/or therapeutic agents. Nucleotide sequences encoding particularly suitable linkers may be, for example, those shown in Table 2.

TABLE 2

Linker Sequences.

| SEQ ID NO: | Description | Nucleotide Length | Sequence |
|---|---|---|---|
| — | 2 aa GS linker | 6 | ggcagc |
| 19 | 6 aa [GS]x linker | 18 | ggtagcggcagcggtagc |
| 20 | 10 aa [GS]x linker | 30 | ggtagcggcagcggtagcggtagcggcagc |
| 21 | 10 aa flexible protein domain linker | 30 | ggtgaaaatttgtattttcaatctggtggt |
| 22 | 8 aa protein domain linker | 24 | tccgcttgttactgtgagctttcc |
| 23 | Split fluorophore linker; Freiburg standard | 51 | cgaccagcctgtaagattccaaatgacctgaagcagaaagttatgaatcac |
| 24 | 15 aa flexible GS linker; Freiburg standard | 45 | ggtggaggaggttctggaggcggtggaagtggtggcggaggtagc |
| 25 | Short Linker (Gly-Gly-Ser-Gly) | 12 | ggtggttctggt |
| 26 | Middle Linker (Gly-Gly-Ser-Gly)x2 | 24 | ggtggttctggtggtggttctggt |
| 27 | Long Linker (Gly-Gly-Ser-Gly)x3 | 36 | ggtggttctggtggtggttctggtggtggttctggt |

TABLE 2-continued Linker Sequences.

| SEQ ID NO: | Description | Nucleotide Length | Sequence |
|---|---|---|---|
| 28 | GSAT Linker | 108 | ggtggttctgccggtggctccggttctggctccagcggtggcagctctg gtgcgtccggcacgggtactgcgggtggcactggcagcggttccggt actggctctggc |
| 29 | SEG-Linker | 108 | ggtggttctggcggcggttctgaaggtggcggctccgaaggcggcgg cagcgagggcggtggtagcgaaggtggtggctccgagggtggcggt tccggcggcggtagc |
| 30 | Z-EGFR-1907_Short-Linker | 192 | gtggataacaaatttaacaaagaaatgtgggcggcgtgggaagaaatt cgtaacctgccgaacctgaacggctggcagatgaccgcgtttattgcga gcctggtggatgatccgagccagagcgcgaacctgctggcggaagc gaaaaaactgaacgatgcgcaggcgccgaaaaccggcggtggttctg gt |
| 31 | Z-EGFR-1907_Middle-Linker | 204 | gtggataacaaatttaacaaagaaatgtgggcggcgtgggaagaaatt cgtaacctgccgaacctgaacggctggcagatgaccgcgtttattgcga gcctggtggatgatccgagccagagcgcgaacctgctggcggaagc gaaaaaactgaacgatgcgcaggcgccgaaaaccggcggtggttctg gtggtggttctggt |
| 32 | Z-EGFR-1907_Long-Linker | 216 | gtggataacaaatttaacaaagaaatgtgggcggcgtgggaagaaattc gtaacctgccgaacctgaacggctggcagatgaccgcgtttattgcgag cctggtggatgatccgagccagagcgcgaacctgctggcggaagcga aaaaactgaacgatgcgcaggcgccgaaaaccggcggtggttctggt ggtggttctggtggtggttctggt |
| 33 | (Gly4Ser)3 Flexible Peptide Linker | 45 | ggtggaggaggctctggtggaggcggtagcggaggcggagggtcg |

Pharmaceutical Formulations

The composition of the present disclosure may also include pharmaceutical formulations. Pharmaceutical formulations may include, for example, pharmaceutically acceptable salts, carriers, adjuvants, vehicles, oils, and lipids as known by those skilled in the art. The pharmaceutical formulations may also be, for example, tablets, capsules, ingestible liquids, powders, liposomes, nanoparticles and controlled release formulations as known by those skilled in the art.

Recombinant Proteins, Vectors, Host Cells and Expression

The compositions of the present disclosure may be prepared as recombinant proteins using recombinant protein expression methods. Suitable polynucleotides may be, for example, SEQ ID NO: 13 (laminin-rEV), SEQ ID NO: 15 (HIV-rEV), and SEQ ID NO: 17 (RVG-rEV). These too permit a degree of variability in their sequence, as for example due to degeneracy of the genetic code, codon bias in favor of the host cell expressing the polypeptide, and conservative amino acid substitutions in the resulting protein. Consequently, the polypeptides and constructs of the invention include not only those which are identical in sequence to the above sequence but also those variant polypeptides with the structural and functional characteristics that remain substantially the same.

Such variants (or "analogs") may have a sequence homology ("identity") of 80%, 90%, 95%, 96%, 97%, 98%, 99%, or more with the reference sequence. In this sense, techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. Programs available such as, for example, BLAST, are capable of calculating both the identity between two polynucleotides and the identity and similarity between two polypeptide sequences, respectively. Other programs for calculating identity or similarity between sequences are known in the art.

The present disclosure is further directed to vectors including nucleic acid sequences encoding the compositions including a neuromuscular junction targeting peptide. The term "vector", as used herein, refers to any recombinant polynucleotide construct that may be used to introduce heterologous DNA into a host cell. Vectors of the present disclosure may further include nucleic acid sequences encoding a neuromuscular junction targeting peptide operably linked to a nucleic acid sequence encoding a therapeutic agent. Vectors of the present disclosure may further include nucleic acid sequences encoding a neuromuscular junction targeting peptide operably linked to a nucleic acid sequence encoding a linker that is further operably linked to a nucleic acid sequence encoding a therapeutic agent.

The compositions of the present disclosure may be produced in prokaryotic and eukaryotic cells using expression vectors suitable for the particular host cell. Particularly suitable prokaryotic cells may be, for example, *Escherichia coli* and *Salmonella* sp. Particularly suitable eukaryotic cells may be, for example, mammalian cells, insect cells, and yeast cells.

The term "construct", as used herein, refers to any recombinant polynucleotide molecule. Examples of constructs may be a plasmid, a cosmid, a virus, an autonomously replicating polynucleotide molecule, a phage, or a linear or circular single-stranded or double-stranded DNA or RNA polynucleotide molecule, derived from any source, capable of genomic integration or autonomous replication, comprising a polynucleotide molecule where one or more polynucleotide molecule(s) has been linked in a functionally operative manner, i.e., operably linked.

As used herein, "operably linked" refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the desired protein. Nucleic acid sequences that can be operably linked may be, for example, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions, sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences). Additional sequences that may be operably linked may be, for example, sequences that facilitate purification of the recombinantly expressed protein such as, for example, affinity tags. Other additional sequences that may be operably linked may be, for example, sequences that encode protease cleavage sites.

An "isolated" polynucleotide (e.g., an "isolated DNA" or an "isolated RNA") refers to a polynucleotide at least partially separated from at least some of the other components of the naturally occurring organism such as, for example, the cell structural components or other polypeptides or nucleic acids commonly found associated with the polynucleotide.

An "isolated" polypeptide refers to a polypeptide that is at least partially separated from at least some of the other components of the naturally occurring organism such as, for example, the cell or structural components or other polypeptides or nucleic acids commonly found associated with the polypeptide.

Once the vector has been constructed by operably linking the components, it may be introduced into a host cell. Operably linking the polynucleotide sequence encoding a neuromuscular junction targeting peptide to a polynucleotide sequence encoding a therapeutic agent and/or a linker, as provided by the present disclosure, results in the production of an expressed polypeptide from the host cell. The vector may be introduced into the host cell by methods known by those skilled in the art. Suitable methods may be, for example, transfection, transformation, and electroporation. The host cell is then cultured under suitable conditions to permit expression of the composition, which is then recovered by isolation and/or purification.

Recombinantly expressed compositions according to the present disclosure may be further isolated and purified according to methods known by those skilled in the art. For example, protein purification may be performed by affinity chromatography, precipitation, chromatography (e.g., affinity, ion exchange, HPLC, gel filtration), extraction, ultrafiltration, electrophoresis, and combinations thereof. Protein isolation and purification may be facilitated by including sequences and amino acid motifs or use of protein expression vectors having sequences and amino acid motifs for affinity purification. Suitable sequences and motifs may be, for example, histidine tags, antigen peptide tags, chitin binding protein, maltose binding protein, glutathione-S-transferase and other suitable tags known by those skilled in the art. Particularly suitable affinity tags may be, for example, histidine tags ("His tags") as illustrated in FIG. 14. As known by those skilled in the art, affinity tags aid in the purification of the protein containing the affinity tag.

Recombinantly expressed compositions according to the present disclosure may further include cleavage sites for proteases to further isolate the composition from other domains. Suitable protease cleavage sites may be any protease cleavage site known by those skilled in the art. Suitable proteases may be, for example, Factor Xa, enterokinase, thrombin, TEV protease (Invitrogen, Carlsbad, Calif.), PRESCISSION (GE Healthcare Life Sciences, Piscataway, N.J.), pepsin cleavage sites, trypsin cleavage sites, chymotrypsin cleavage sites, thermolysin cleavage sites, and other protease cleavage sites known by those skilled in the art. Particularly suitable protease cleavage sites may be, for example, a thrombin cleavage site.

Additionally or alternatively, the compositions of the present disclosure may be prepared using chemical synthesis methods. Suitable chemical synthesis methods are well-known in the art and may include, for example, liquid-phase peptide synthesis, solid-phase peptide synthesis, fragment condensation, and chemical ligation.

Methods for Delivering a Therapeutic Agent to the Neuromuscular Junction

In another aspect, the present disclosure is directed to a method for delivering a therapeutic agent to the neuromuscular junction. The method includes administering a composition including a neuromuscular junction targeting peptide coupled to a therapeutic agent.

The neuromuscular junction targeting peptide may be any neuromuscular junction targeting peptide as described herein. The therapeutic agent may be any therapeutic agent as described herein. The composition may further include at least one linker as described herein.

Administration may be to a subject. Suitable methods for administration to a subject may be, for example, by intravenous injection, intravenous infusion, intraperitoneal injection, intradermal injection, intramuscular injection, subcutaneous injection, intranasal, oral, and other methods known by those skilled in the art. Administration may also be to a cell in culture. Suitable methods for administration to a cell in culture may also, for example, by pipetting, pouring a solution containing the composition, and other methods know in the art.

Dosage of the composition to be administered may be determined by those skilled in the art. Dosage may depend on various factors such as, for example, the condition or disease, weight of the subject, age of the subject, method of administration, route of administration, whether administered for an in vivo purpose, whether administered for an in vitro purpose, and other factors. The dosage to a subject will generally include an amount that is sufficient to provide some improvement or benefit to the subject so as to provide some alleviation, mitigation, or decrease in at least one clinical symptom in the subject. The dosage may also include an amount that is sufficient to provide an in vitro complement inhibitory effect or prevention of complement-dependent cell lysis, for example.

Suitable dosages may be from about 0.001 µg/ml to about 4 µg/ml. Particularly suitable dosages may be from about 0.001 µg/ml to about 0.02 µg/ml. Suitable dosages may be determined in vitro, for example, by investigating the inhibition of complement hemolytic activity of antibody sensitized erythrocytes, by luminescent bioassay of antibody-initiated, complement mediated injury of cell lines (for example, the toxilight bioassay commercially available from Cambrex, Rockland, Me.). Suitable dosages may also be determined in vivo, for example, by analyzing targeting to the neuromuscular junction, analyzing the production of weakness in the subject, and determining alterations in systemic complement activity. Those skilled in the art will appreciate that the therapeutic effects need not be complete or curative, as long as some benefit is provided to the subject.

Methods for Treating Neuromuscular Junction-Related Diseases or Conditions

In another aspect, the present disclosure is directed to a method for treating a neuromuscular junction-related disease or condition. The method includes administering to a subject in need thereof a composition including a neuromuscular junction targeting peptide coupled to a therapeutic agent.

As used herein "neuromuscular junction-related diseases or conditions" refer to diseases or conditions resulting from injury at and/or to the neuromuscular junction. A neuromuscular junction-related disease or condition may be, for example, myasthenia gravis, experimentally acquired myasthenia gravis, Lambert-Eaton syndrome, Miller Fischer syndrome, congenital myasthenic syndromes, botulism, organophosphate poisoning, and other toxins that compromise the neuromuscular junction.

The methods include the administration of the compositions to a subject in need thereof including individuals afflicted with neuromuscular junction-related diseases or conditions resulting from injury at and/or to the neuromuscular junction as described herein. Additionally, a subject in need thereof includes laboratory animals experimentally induced to mimic diseases or conditions resulting from injury at and/or to the neuromuscular junction, thus serving as animal models of these diseases and conditions. As such, in some embodiments of the present disclosure, the methods disclosed herein are directed to a subset of the general population such that not all of the general population may benefit from these methods.

Suitable subjects may be mammals. Suitable mammals may be, for example, humans, mice, rats, rabbits, guinea pigs, and monkeys.

The neuromuscular junction targeting peptide may be any neuromuscular junction targeting peptide described herein. The therapeutic agent may be any therapeutic agent as described herein. The composition may further include at least one linker as described herein.

Suitable methods for administration may be, for example, by intravenous injection, intravenous infusion, intraperitoneal injection, intradermal injection, intramuscular injection, subcutaneous injection, intranasal, oral, and other methods known by those skilled in the art.

Suitable therapeutically effective amounts may be, for example, from about 1 ng/kg to about 0.1 mg/kg. More particularly, the therapeutically effective amount may be about 5 mg/kg. Suitable therapeutically effective amounts may further be described as having a half maximal inhibitory concentration ($IC_{50}$) of from about 0.001 µg/ml to about 40 µg/ml. A particularly suitable $IC_{50}$ may be from about 10 ng/ml to about 20 µg/ml. The therapeutically effective amount may be characterized, for example, by observing a prolonged biological effect without observation of the production of weakness in the subject. The therapeutically effective amount of the composition to be administered to the subject may be determined by those skilled in the art. The therapeutically effective amount may depend on various factors such as, for example, the condition or disease, weight of the subject, age of the subject, method of administration, route of administration, and other factors. Generally, the therapeutically effective amount will include an amount that is sufficient to provide some improvement or benefit to the subject so as to provide some alleviation, mitigation, or decrease in at least one clinical symptom in the subject. Those skilled in the art will appreciate that the effect need not be complete or curative, as long as some benefit is provided to the subject.

The disclosure will be more fully understood upon consideration of the following non-limiting Examples.

EXAMPLES

Example 1

L-rEV Cloning and Expression

In this Example, a composition including the neuromuscular junction targeting peptide obtained from laminin (encoded by SEQ ID NO: 1) coupled to rEV (encoded by SEQ ID NO: 10) was prepared by recombinant protein expression.

Specifically, the laminin neuromuscular junction targeting peptide was coupled to rEV. As shown in FIG. 1, the construct further included a linker, a His tag and a thrombin cleavage site. Codon optimization was performed using the codon optimization program available from Integrated DNA Technologies.

The cDNA encoding laminin-linker-rEV was subcloned into the prokaryotic expression vector plasmid pET-28-a(+) via NheI and EcoRI sites within multi-cloning sites. The plasmid was verified by restriction enzyme analysis and direct sequencing. A schematic of the plasmid construct is shown in FIG. 2.

For recombinant protein expression of the laminin-linker-rEV, BL21 *E. coli* were transformed with the pET28a-laminin-linker-rEV plasmid prepared above and induced with 1 mM 1 mM isopropyl-β-D-thiogalactopyranoside (IPTG) for 4 hrs. Cells were lysed by sonication in lysis buffer containing 3.2 mM $Na_2HPO_4$, 0.5 mM $KH_2PO_4$, 1.3 mM KCl, 135 mM NaCl, pH 7.4, 5 mM imidazole, lysozyme and protease inhibitor tablet (Roche). After centrifugation at 13,000 rpm at 4° C. for 20 minutes, the soluble fraction was applied to a Talon metal affinity column (Clontech), washed with buffer A (3.2 mM Na$_2$HPO$_4$, 0.5 mM KH$_2$PO$_4$, 1.3 mM KCl, 135 mM NaCl, pH 7.4) and eluted with buffer A containing different concentrations of Imidazole (20 mM to 500 mM). The fractions containing the protein of interest were pooled and concentrated using Amicon ultra 10K MWCO filters (Millipore). The concentrated protein was then applied onto a Superdex200 column (GE healthcare) for gel filtration chromatography. The eluted fractions were analyzed for the presence of protein and concentration of positive fractions was undertaken. The resultant protein was stored at −80° C. or used for further experimentation.

Figure 3:
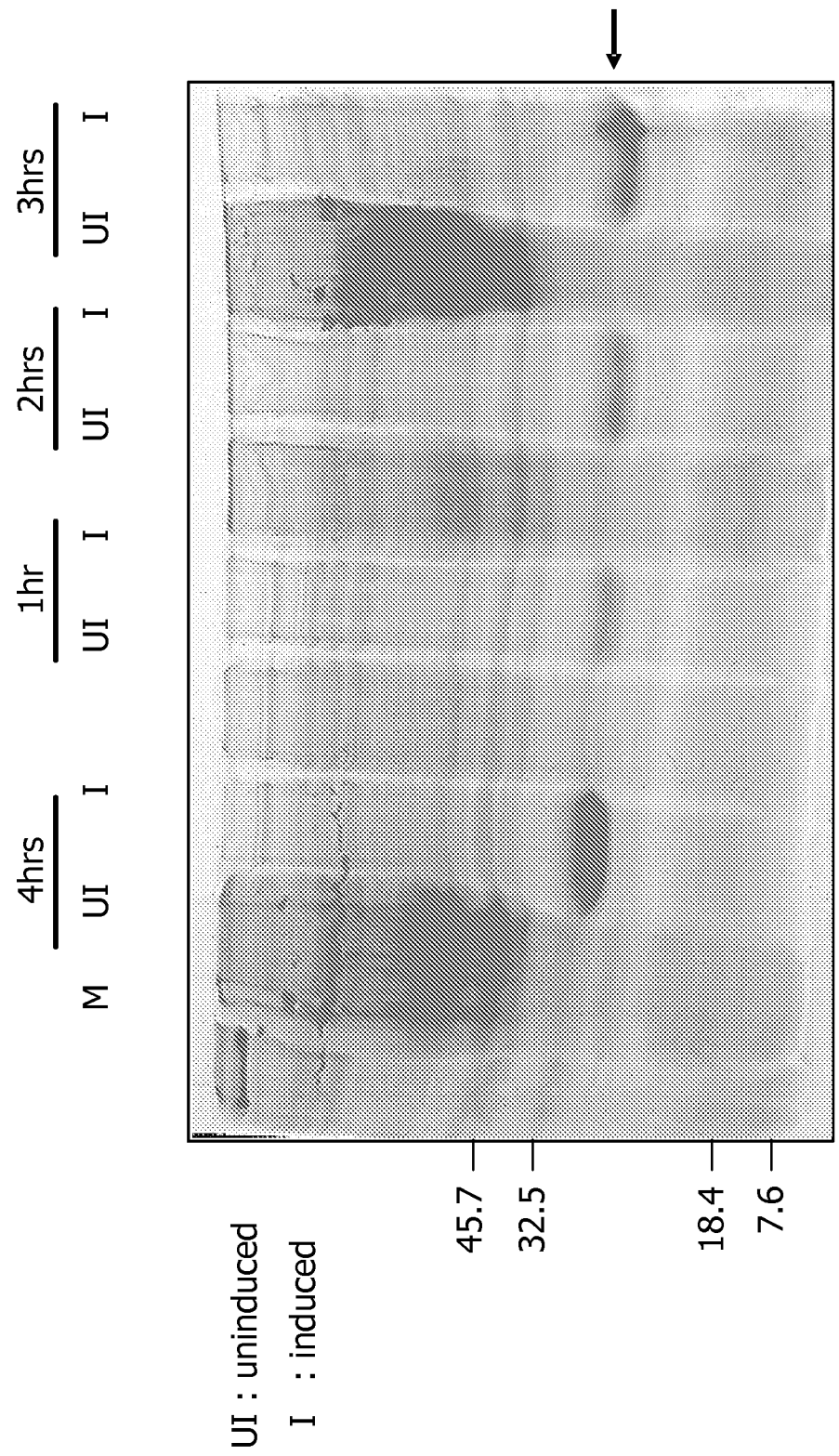
FIG. 3 is an SDS-gel showing the expression of the laminin-rEV polypeptide in BL21 as described in Example 1.
Figure 4:
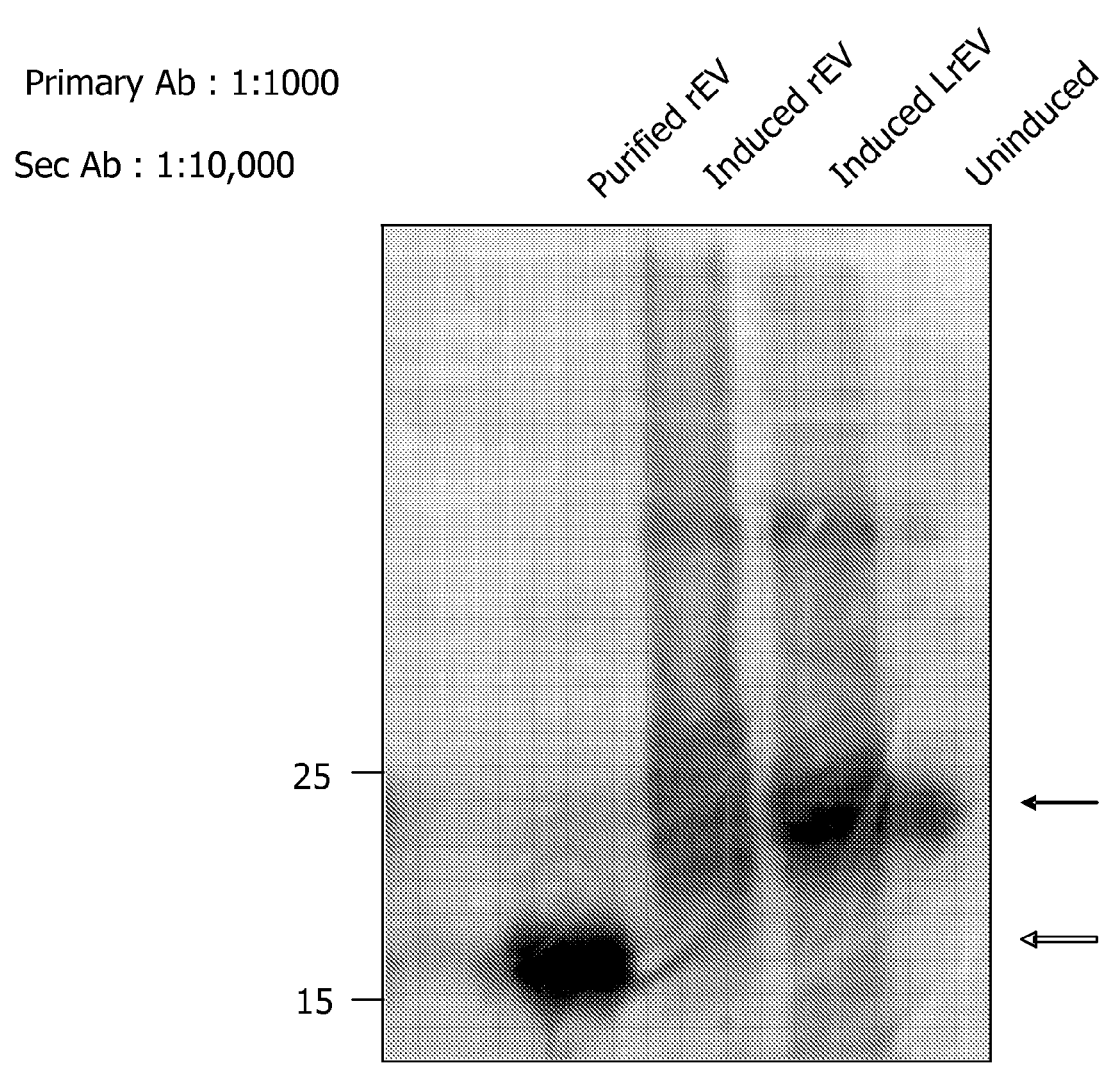
FIG. 4 is a Western blot of purified rEV, expressed rEV from induced cells, expressed laminin-rEV (LrEV) from induced cells, and uninduced cells.

Concentration of the purified protein was determined by the Bradford assay. As shown in FIG. 3, induced BL21 cells began expressing laminin-rEV within 1 hour after induction with maximal expression at 4 hours. Western blot analysis using an anti-rEV antibody confirmed expression in induced cells. See, FIG. 4.

Example 2

HIV-rEV

In this Example, a composition including the neuromuscular junction targeting peptide from HIV (encoded by SEQ ID NO: 3) coupled to rEV (encoded by SEQ ID NO: 10) was prepared as set forth in Example 1.

Figure 5:
FIG. 5 is a schematic showing the domain structure of the HIV-rEV polypeptide as described in Example 2.

Specifically, the HIV neuromuscular junction targeting peptide was coupled to rEV. As shown in FIG. 5, the construct further included a linker, a His tag and a thrombin cleavage site. Codon optimization was performed using the codon optimization program available from Integrated DNA Technologies.

BL21 *E. coli* were transformed with the pET28a-HIV-linker-rEV plasmid and induced with IPTG for 4 hours. Cells were lysed and the protein was purified as set forth in Example 1 above. The resultant protein was stored at −80° C. or used for further experimentation.

Example 3

RVG-rEV

In this Example, a composition including the neuromuscular junction targeting peptide obtained from RVG (encoded by SEQ ID NO: 5) coupled to rEV (encoded by SEQ ID NO: 10) was prepared as set forth in Example 1.

Figure 6:
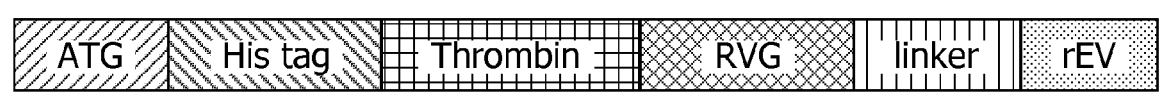

Specifically, the RVG neuromuscular junction targeting peptide was coupled to rEV. As shown in FIG. 6, the construct further included a linker, a His tag and a thrombin cleavage site. Codon optimization was performed using the codon optimization program available from Integrated DNA Technologies.

BL21 *E. coli* were transformed with the pET28a-RVG-linker-rEV plasmid and induced with IPTG for 4 hours. Cells were lysed and the protein was purified as set forth in Example 1 above. The resultant protein was stored at −80° C. or used for further experimentation.

Example 4

In this Example, a composition including the neuromuscular junction targeting peptide using the single chain antibody fragment (scFv) obtained from Mab 35 coupled to decay accelerating factor (DAF) was prepared as set forth in Example 1.

Figure 7:
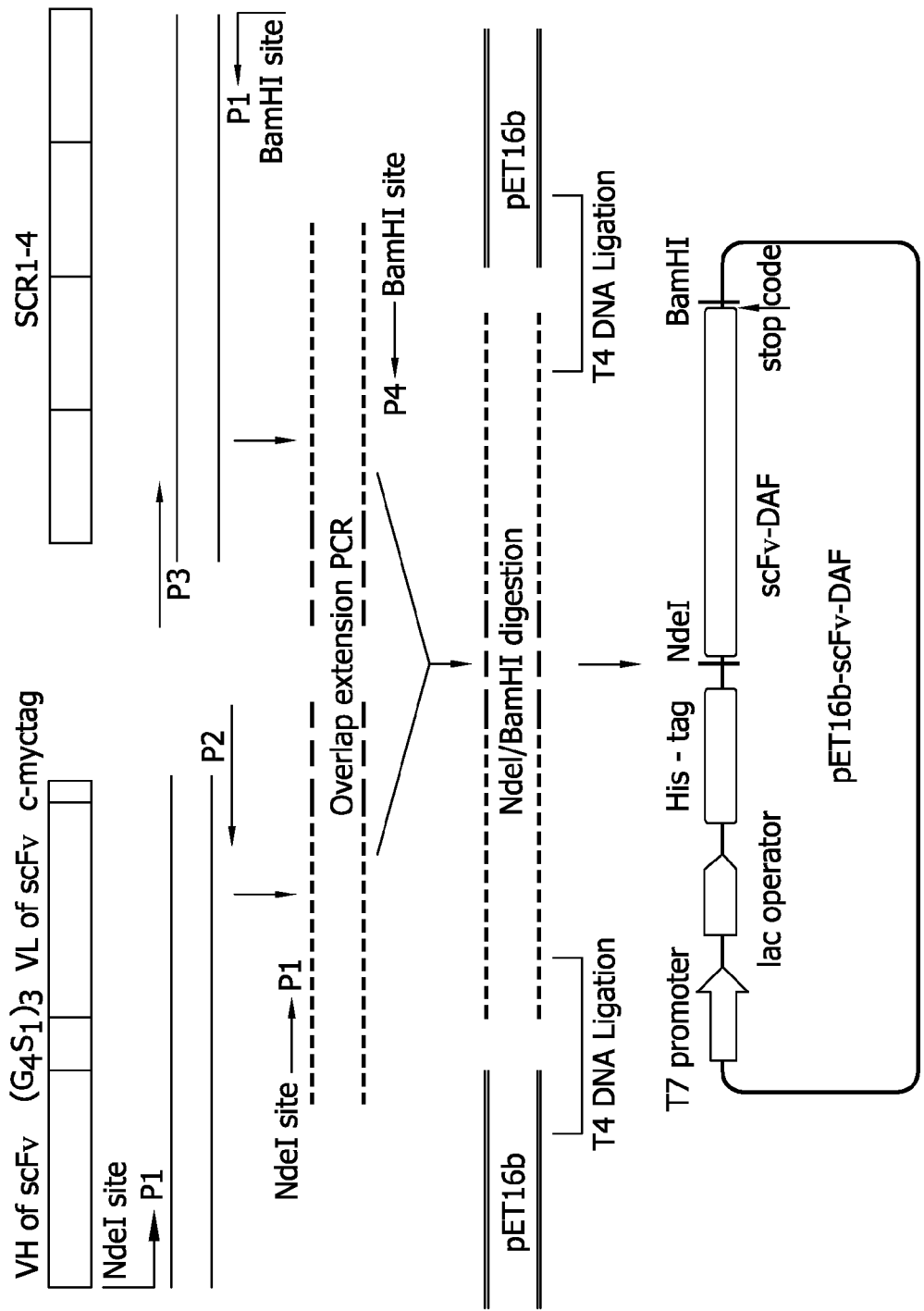
FIG. 7 is a schematic showing the construction of the pET16b-scFv-DAF expression vector as described in Example 4.
Figure 8:
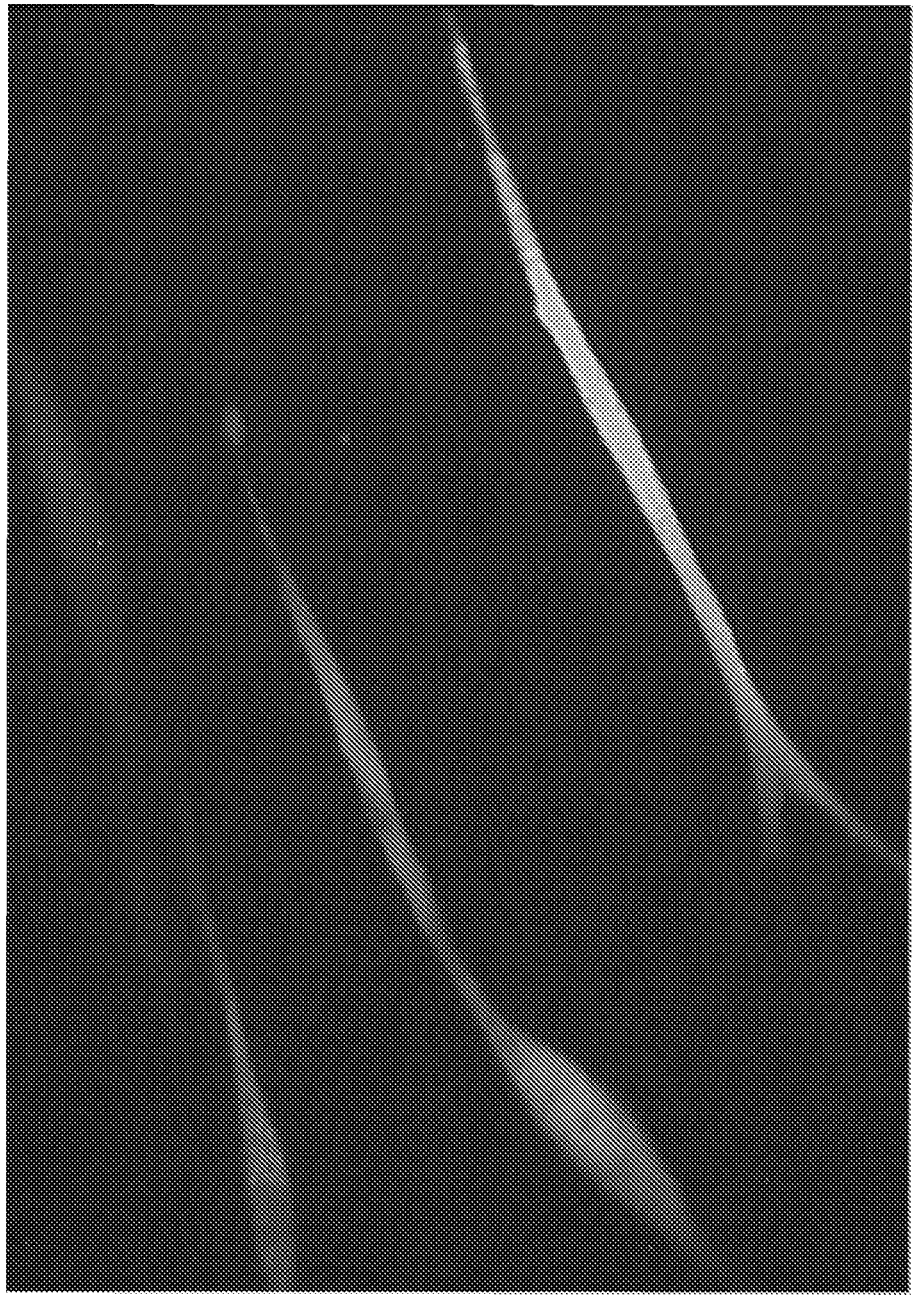
FIG. 8 is a photomicrograph showing GFP expression in BHK-21 cells transfected with the IgGsp-$V_H$-$V_L$ as described in Example 4.

Specifically, the scFv was fused to DAF and inserted into the pET16b expression vector as outlined in FIG. 7. To generate the $V_H$-$V_L$ fragment of the scFv, RNA was obtained from the TIB-175 hybridoma cell line (obtained from ATCC), which secretes the Mab 35 antibody. The variable heavy chain ($V_H$) and/or variable light chain ($V_L$) were the amplified by RT-PCR. Overlapping PCR was used to generate the $V_H$-$V_L$ fragment with the (GGGGS)$_3$ (SEQ ID NO: 34) linker to produce the single chain AChR antibody scFv. Sequencing confirmed the identity of the cloned fragments as $V_H$ and $V_L$ regions. Two signaling peptide constructs were then produced using the CD59 fragment or the IgG signal peptide. The CD59sp- or IgGsp-signaling peptide was then fused to the $V_H$-$V_L$ fragment and cloned into the pIRES2-AcGFP1 vector (Clonetech, Mountain View, Calif.). BHK-21 cells were transfected with these constructs. FIG. 8 shows expression of GFP by transfected BHK-21 cells transfected with the IgG $V_H$-$V_L$ fragment.

DAF was then fused to either the CD59sp-$V_H$-$V_L$ or IgGsp-$V_H$-$V_L$. The CD59sp-$V_H$-$V_L$-DAF is a 537 amino acid peptide (SEQ ID NO: 34). The IgGsp-$V_H$-$V_L$-DAF is a 534 amino acid peptide (SEQ ID NO: 35).

Figure 9:
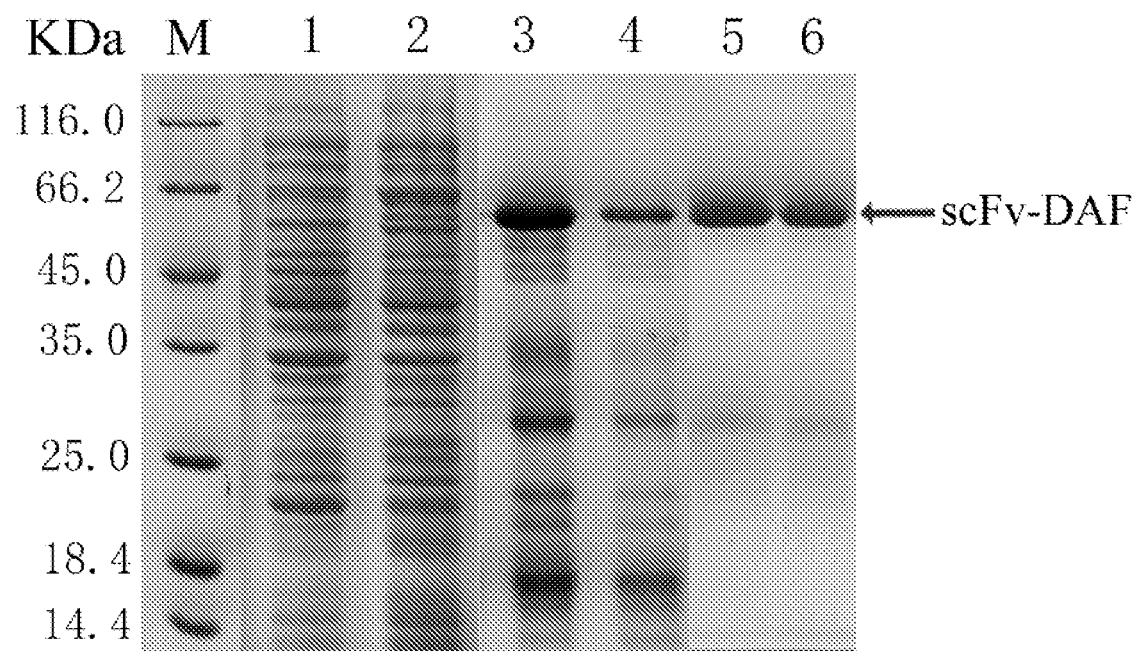

BL21 cells were transformed with the pET16b expression vector containing the scFv-DAF construct as previously described. Expressed protein was purified using a Hitrap chelating HP column (manufacturer) and refolded by urea gradient dialysis. Samples taken during the expression, purification, and refolding steps were analyzed by SDS-PAGE. See, FIG. 9. Lane 1 is a sample of the pET16b-scFv-DAF/BL21 before induction; lane 2 is a sample of the pET16b-scFv-DAF/BL21 after induction; lanes 3 and 4 are eluted peaks of the fusion protein from Hitrap chelating HP columns; lanes 5 and 6 are refolded fusion protein after urea gradient dialysis; lane M is molecular weight markers.

Example 5

Figure 10:
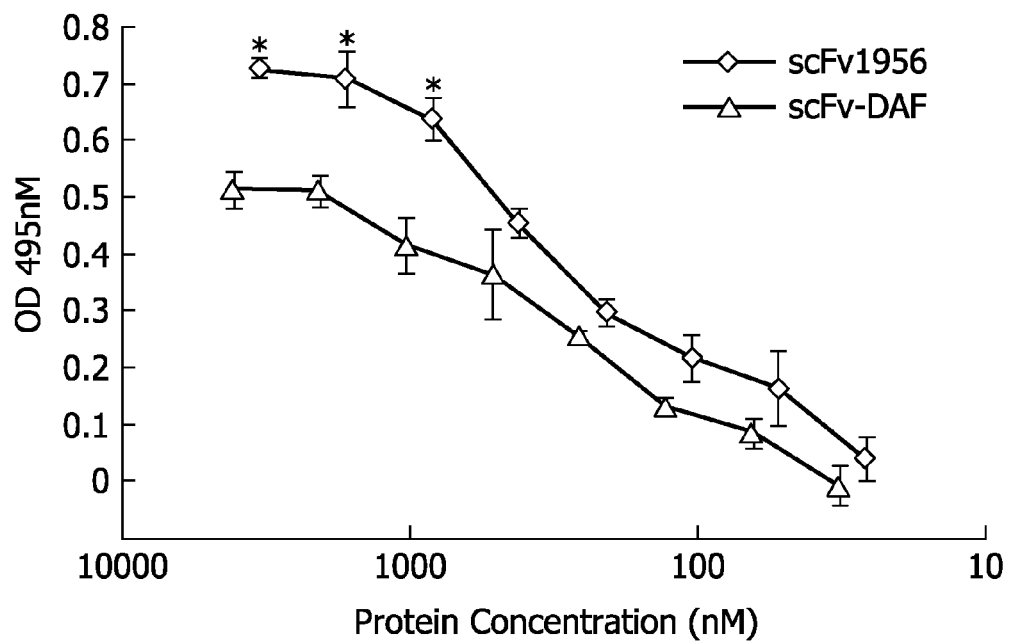
FIG. 10 is a graph showing the specificity binding of scFv-DAF and scFv1956 to hAChRα1-210 polypeptides as described in Example 5.

The scFv-DAF fusion protein was analyzed for specificity binding to hAChRα1-210 peptides by ELISA.

hAChRα1-210 peptides (2 μg/ml) were coated on plates and incubated with serially diluted scFv-DAF or scFv1956. Results were expressed in ODs. Results are presented in FIG. 10. Values represented the mean±SD. *P<0.05.

Example 6

The scFv-DAF fusion protein was analyzed for in vitro complement regulatory function.

Figure 11:
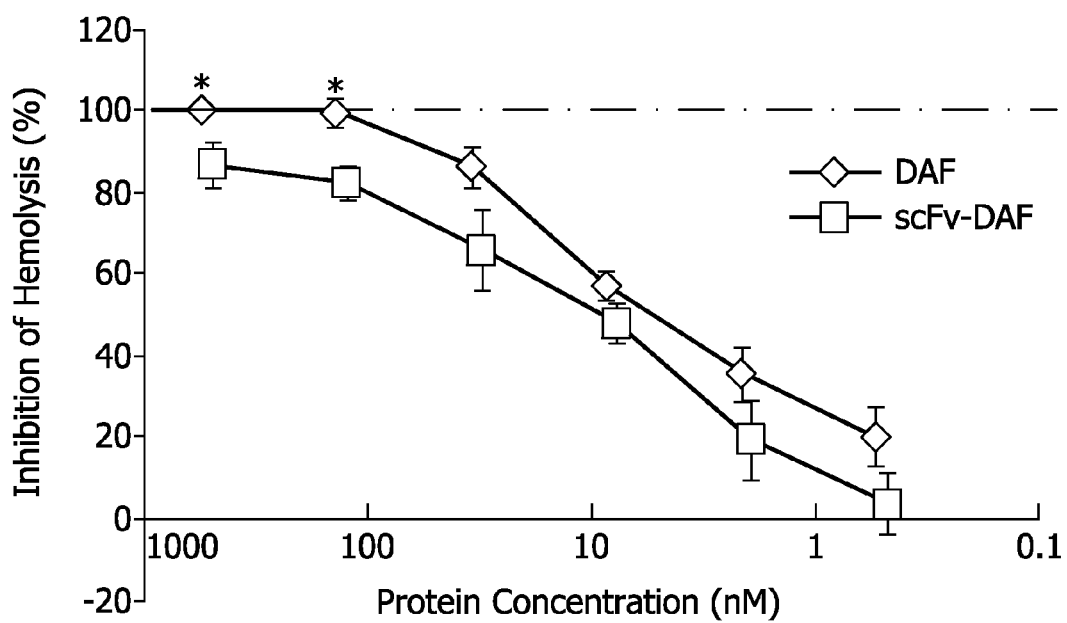
FIG. 11 is a graph showing complement-mediated haemolysis of sheep erythrocytes incubated with scFv-DAF as described in Example 6.

Antibody-sensitized sheep erythrocytes were used as target. The degree of complement-mediated haemolysis was quantified by the release of haemoglobin to the supernatant and plotted as molar concentration of inhibitor present in the assay. Results represent the man value±SD of experiments carried out in triplicate. Results are presented in FIG. 11. *P0.05.

Example 7

In this Example, targeting of scFv-35-DAF to the neuromuscular junction was analyzed.

The scFv-35-DAF prepared in Example 6 was injected into C57/Black 6 and CD59−/−, DAF−/− mice, which are highly susceptible to complement injury. After 24 hours weight and weakness were assessed. The animals were found to gain weight and exhibited no loss of strength indicating the scFv-35-DAF did not inhibit neuromuscular junction transmission.

Figure 12:
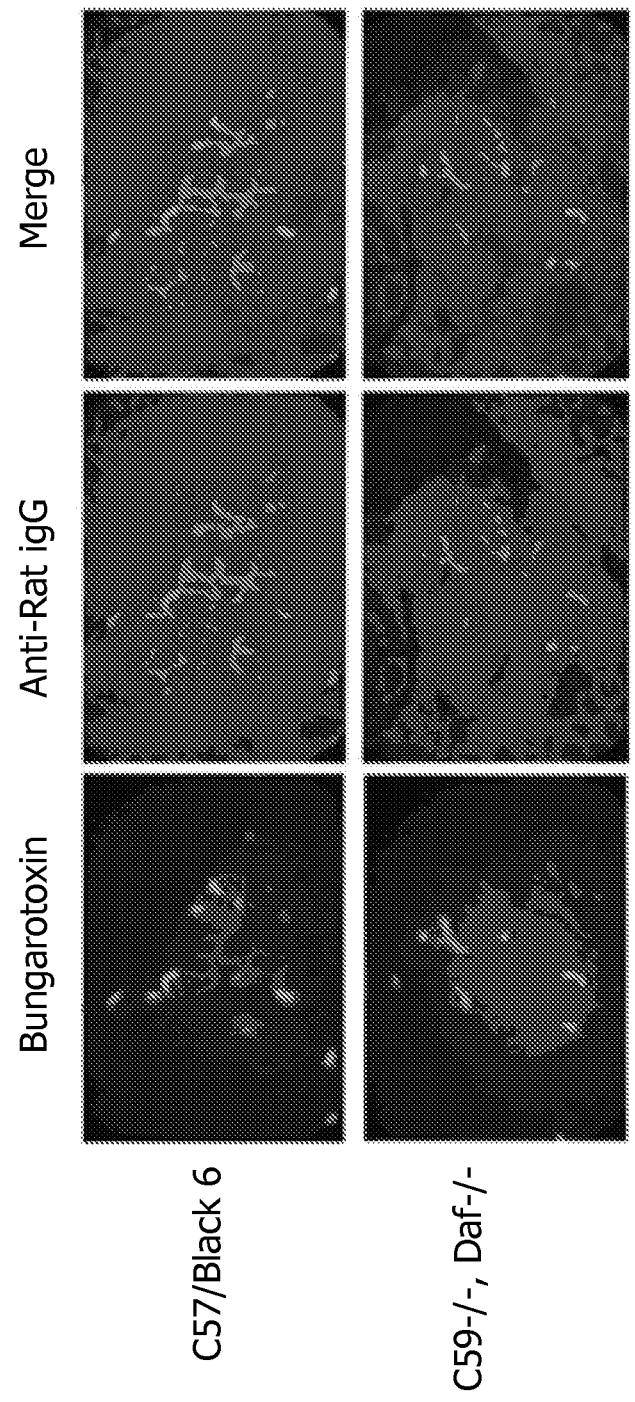
FIG. 12 are photomicrographs showing localization of the scFv-35-DAF to the neuromuscular junction in diaphragms of mice as described in Example 7.

Diaphragms were used to visualize localization of the scFv-35-DAF to the neuromuscular junction by the anti-Rat IgG and Bungarotoxin to identify junctions. As shown in FIG. 12, the scFv-35-DAF was localized to the neuromuscular junction in both animals and there was no evidence of tissue destruction, even in the complement regulator deficient mouse. These results confirmed that the scFv-35-DAF construct is safe and specifically targets to the neuromuscular junction.

The scFv-35-DAF was also administered to Lewis rats. The acetylcholine receptor antibody was administered to the Lewis rats 24 hours later to induce experimental myasthenia gravis. At 48 hours, the severity of weakness was maximal in control rats. Of five animals treated with scFv-35-DAF, all survived and showed mild-to-moderate weakness. In the rats treated with scFv-35, 3 animals died and 2 had severe weakness. These results indicated that scFv-35-DAF was safe and has a robust protective effect.

Example 8

In this Example, the affect of scFv-35-DAF on the deposit of C3 on TE671 cells was analyzed.

TE671 cells were treated with normal basal medium with scFv-DAF, scFv1956, and DAF (100 nM). Negative controls were treated with PBS in place of mAb35. Cells were stained with FITC-conjugated anti-C3 antibody and stained with Eosin staining solution as contrast stain. Images were obtained at 200× (Panels A-E), 400× (Panels F-J), and 1000× (Panels K-0). Cells were also analyzed by flow cytometry.

Figure 13:
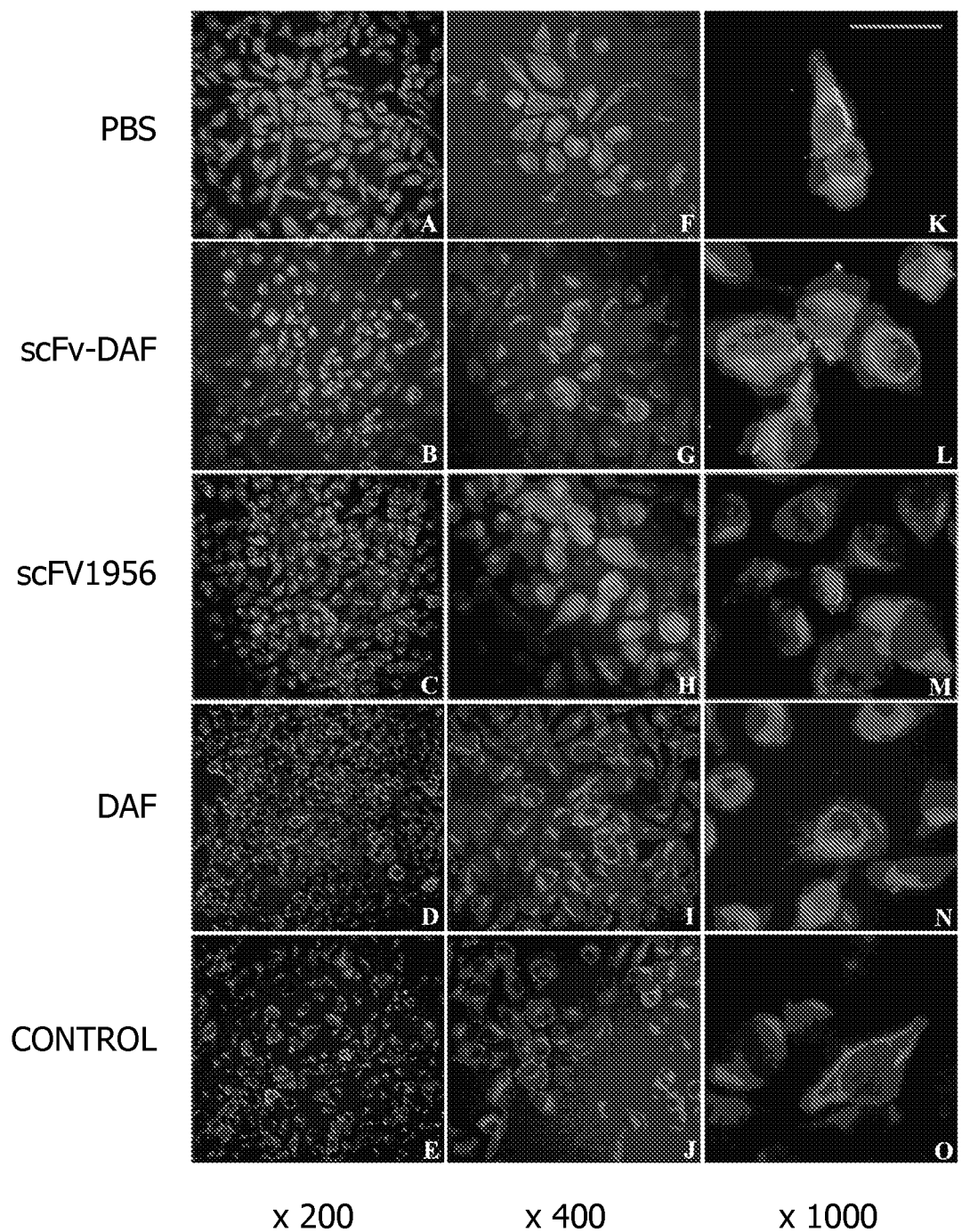
FIG. 13 shows immunofluorescence micrographs showing scFv-DAF reduction of C3 deposits on TE671 cells as described in Example 8.

Results are presented in FIG. 13. Staining of C3 deposited on cells treated with scFv-DAF and scFv1956 was patchy and moderate (see, Panels L and M). The staining of C3 deposits around TE671 cells was diffuse (see, Panels M, N, and O). Scale bar=10 μm.

Results demonstrated that scFv-DAF fusion protein inhibits its C3 deposition on the TE671 cell surface.

Example 9

In this Example, the therapeutic effect of scFv-35-DAF in EAMG mice and rats was analyzed.

Figure 15:
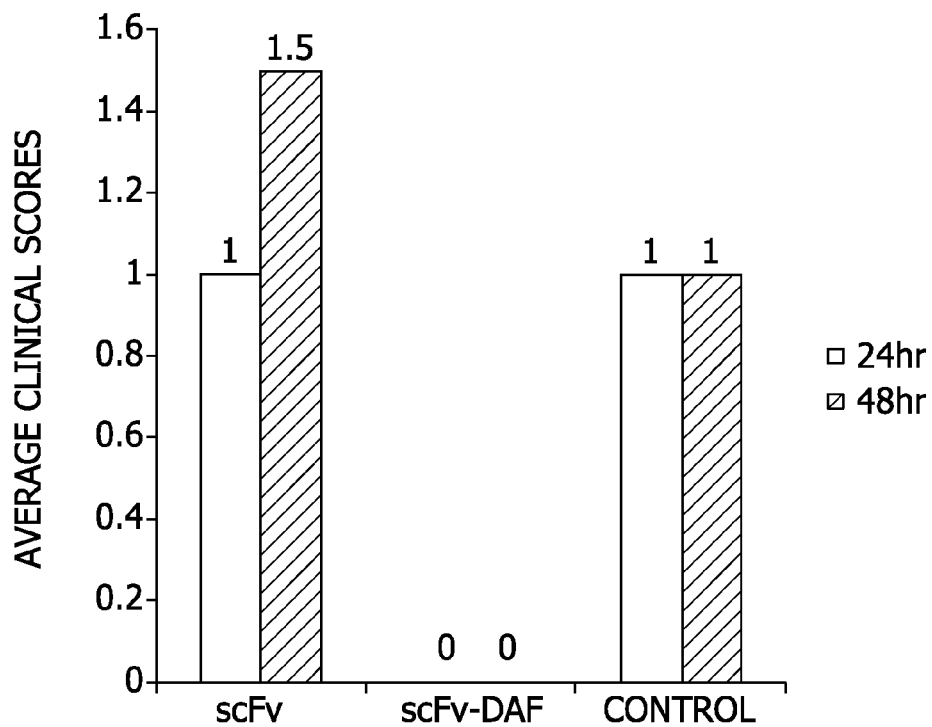
FIG. 15 is a graph depicting the therapeutic effect of scFv and scFv-DAF in EAMG mice as described in Example 9.
Figure 16:
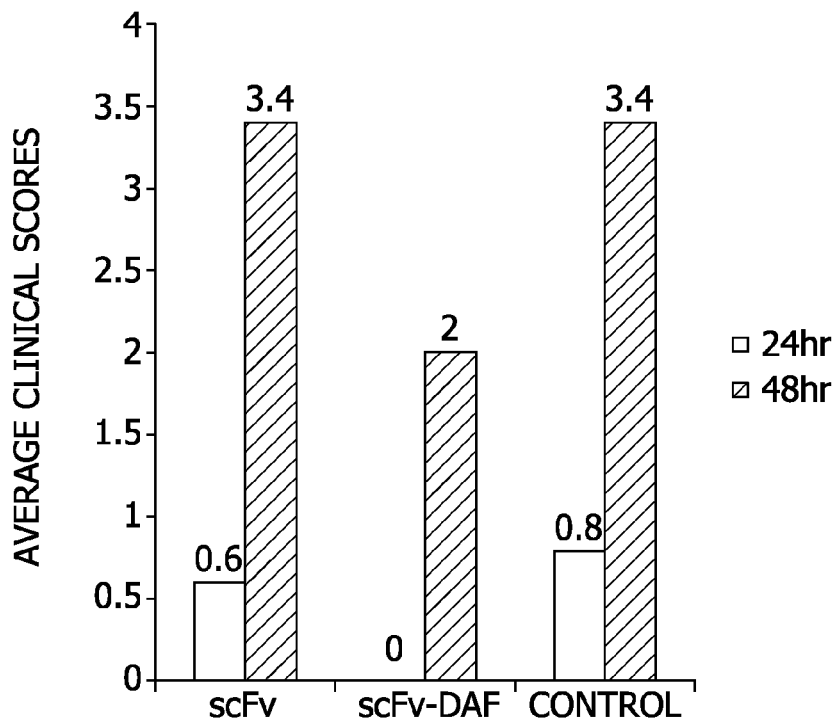
FIG. 16 is a graph is a graph depicting the therapeutic effect of scFv and scFv-DAF in EAMG Lewis rats as described in Example 9.

Specifically, EAMG was induced in DAF−/−, CD59ab−/− mice and Lewis rats followed by treatment with scFv, scFv-DAF, and PBS (as a control). All mice showed no evidence of disease (see FIG. 15), while rats treated with scFv-DAF showed significant protection from EAMG (FIG. 16). Quantitative analysis of complement deposition demonstrated significantly less MAC deposition at endplates of scFv-Daf-treated animals compared to both vehicle- and scFv-treated rats. In comparing the scFv and the vehicle, the scFv had a marginally significant increase in complement deposition. Consistent with the better clinical outcome, AChR density was significantly better in the scFv-DAF-treated rats than scFv and vehicle treated rats (not shown).

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A composition comprising a neuromuscular junction targeting peptide coupled to a therapeutic agent, wherein the neuromuscular junction targeting peptide is selected from the group consisting of SEQ ID NO: 2, SEQ ID NO: 7, SEQ ID NO: 8, and SEQ ID NO: 9 and wherein the therapeutic agent is selected from the group consisting of a complement inhibitor, an acetylcholinesterase inhibitor, and a trophic agent.

2. The composition of claim 1, wherein the complement inhibitor is selected from the group consisting of decay accelerating factor, rEV encoded by SEQ ID NO: 10, rEV576, membrane cofactor protein, compstatin, a compstatin derivative, POT-4, a C1 inhibitor, C4b-binding protein, factor H, complement receptor Ig, CD59 (complement regulatory protein), clusterin, a C3-inhibitor, peptide 2J (SEQ ID NO: 36), human beta-defensin 2, CRIT-H17 (C2 receptor inhibitor trispanning-H17), Ac-SHLGLAR-H (SEQ ID NO: 37), Ac-RLLLAR-H (SEQ ID NO: 38), C1s-INH-248 (synthetic small molecule inhibitor of C1s), S-protein, Crry (complement receptor related protein), circumin, W-54011 (N-((4-Dimethylaminophenyl)methyl)-N-(4-isopropylphenyl)-7-methoxy-1,2,3,4-tetrahydronaphthalen-1-carboxamide), NDT9520492 ((2S)—N-(2,3-dihydro-1H-inden-2-yl)-N-[(2-fluorophenyl)methyl]-2-[(1R)-1-naphthalen-1-yl-3,4-dihydro-1H-isoquinolin-2-yl]propanamide), CP-447697 (4-{(1-Benzothiophen-3-ylcarbonyl)[2-(4-chlorophenyl)ethyl]amino}-N-(2,4-difluorophenyl)-1-piperidinecarboxamide), NDT 9513727 ([N,N-bis(1,3-benzodioxol-5-ylmethyl)-1-butyl-2,4-diphenyl-1H-imidazole-5-methanamine]), SB290157 (N²-[(2,2-Diphenylethoxy)acetyl]-L-arginine, SB290157(A) (arginine-substituted SB290157), SB290157(B) (aminopiperidine-derivative SB290157), BCX1470 (2-amidino-6-[2-thiophene carboxyl]benzothiophene methanesulfonate), PMX53 ((25)-2-acetamido-N-[(3S,9S,12S,15R,18S)-15-(cyclohexylmethyl)-9-[3-(diaminomethylideneamino)propyl]-12-(1H-indol-3-ylmethyl)-2,8,11,14,17-pentaoxo-1,7,10,13,16-pentazabicyclo[16.3.0]henicosan-3-yl]-3-phenylpropanamide), PMX205 (hydrocinnamic acid substituted derivative of PMX53), C089 (NMe-Phe-Lys-Pro-D-Cha-Trp-D-Arg-COOH), and JPE1375 (hydroorotic acid-Phe-Orn-Pro-(d-HomoLeu)-(4-Fluoro-Phe)-Phe).

3. The composition of claim 1, further comprising a linker.

4. The composition of claim 3, wherein the linker is selected from the group consisting of a glycine-serine linker, a peptide encoded by SEQ ID NO: 19, a peptide encoded by SEQ ID NO: 20, a peptide encoded by SEQ ID NO: 21, a peptide encoded by SEQ ID NO: 22, a peptide encoded by SEQ ID NO: 23, a peptide encoded by SEQ ID NO: 24, a peptide encoded by SEQ ID NO: 25, a peptide encoded by SEQ ID NO: 26, a peptide encoded by SEQ ID NO: 27, a peptide encoded by SEQ ID NO: 28, a peptide encoded by SEQ ID NO: 29, a peptide encoded by SEQ ID NO: 30, a peptide encoded by SEQ ID NO: 31, a peptide encoded by SEQ ID NO: 32, and a peptide encoded by SEQ ID NO: 33.

5. A method of delivering a therapeutic agent to the neuromuscular junction, the method comprising:
administering the composition according to claim 1 comprising a neuromuscular junction targeting peptide coupled to a therapeutic agent.

6. A composition comprising a neuromuscular junction targeting peptide coupled to a complement inhibitor, wherein the neuromuscular junction targeting peptide is selected from the group consisting of SEQ ID NO: 2, SEQ ID NO: 7, SEQ ID NO: 8, and SEQ ID NO: 9 and wherein the complement inhibitor is selected from the group consisting of decay accelerating factor, rEV encoded by SEQ ID NO: 10, rEV576, membrane cofactor protein, compstatin, a compstatin derivative, POT-4, a C1 inhibitor, C4b-binding protein, factor H, complement receptor Ig, CD59, clusterin, a C3-inhibitor, peptide 2J (SEQ ID NO: 36), human beta-defensin 2, CRIT-H17, Ac-SHLGLAR-H (SEQ ID NO: 37), Ac-RLLLAR-H (SEQ ID NO: 38), C1s-INH-248, S-protein, Crry, circumin, W-54011, NDT9520492, CP-447697, NDT 9513727, SB290157, SB290157(A), SB290157(B), BCX1470, PMX53, PMX205, C089, and JPE1375.

7. The composition of claim 6, further comprising a linker.

8. The composition of claim 7, wherein the linker is selected from the group consisting of a glycine-serine linker, a peptide encoded by SEQ ID NO: 19, a peptide encoded by SEQ ID NO: 20, a peptide encoded by SEQ ID NO: 21, a peptide encoded by SEQ ID NO: 22, a peptide encoded by SEQ ID NO: 23, a peptide encoded by SEQ ID NO: 24, a peptide encoded by SEQ ID NO: 25, a peptide encoded by SEQ ID NO: 26, a peptide encoded by SEQ ID NO: 27, a peptide encoded by SEQ ID NO: 28, a peptide encoded by SEQ ID NO: 29, a peptide encoded by SEQ ID NO: 30, a peptide encoded by SEQ ID NO: 31, a peptide encoded by SEQ ID NO: 32, and a peptide encoded by SEQ ID NO: 33.

* * * * *

SEQUENCE LISTING

<160> NUMBER OF SEQ ID NOS: 38

<210> SEQ ID NO 1
<211> LENGTH: 60
<212> TYPE: DNA
<213> ORGANISM: Artificial Sequence
<220> FEATURE:
<223> OTHER INFORMATION: Synthetic

<400> SEQUENCE: 1
gaacagcaga ccgcagacca actcctagcc cgagctgatg ctgccaaggc cctcgctgaa        60

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Glu Gln Gln Thr Ala Asp Gln Leu Leu Ala Arg Ala Asp Ala Ala Lys
1               5                   10                  15

Ala Leu Ala Glu
            20

<210> SEQ ID NO 3
<211> LENGTH: 33
<212> TYPE: DNA

```
<213> ORGANISM: Artificial Sequence
<220> FEATURE:
<223> OTHER INFORMATION: Synthetic

<400> SEQUENCE: 3
tttaacatta gcaccagcat tcgcggcaaa gtg                            33

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Phe Asn Ile Ser Thr Ser Ile Arg Gly Lys Val
1               5                   10

<210> SEQ ID NO 5
<211> LENGTH: 33
<212> TYPE: DNA
<213> ORGANISM: Artificial Sequence
<220> FEATURE:
<223> OTHER INFORMATION: Synthetic

<400> SEQUENCE: 5
tgcgatattt ttaccaacag ccgcggcaaa cgc                            33

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Cys Asp Ile Phe Thr Asn Ser Arg Gly Lys Arg
1               5                   10

<210> SEQ ID NO 7
<211> LENGTH: 277
<212> TYPE: PRT
<213> ORGANISM: Artificial Sequence
<220> FEATURE:
<223> OTHER INFORMATION: Synthetic

<400> SEQUENCE: 7

Met Arg Ala Gln Arg Gly Leu Ile Leu Leu Leu Leu Leu Ala Val
1               5                   10                  15

Phe Cys Ser Thr Ala Val Ser Leu Thr Val Lys Leu Gln Glu Ser Gly
                20                  25                  30

Pro Gly Leu Val Gln Pro Ser Glu Thr Leu Ser Leu Thr Cys Thr Val
        35                  40                  45

Ser Gly Phe Ser Leu Thr Ser Tyr Ser Val Ser Trp Leu Arg Gln Pro
    50                  55                  60

Ser Gly Lys Gly Pro Glu Trp Met Gly Arg Met Trp Asp Asp Gly Gly
65                  70                  75                  80

Thr Val Tyr Asn Ser Gly Leu Lys Ser Arg Leu Ser Ile Ser Arg Asp
                85                  90                  95

Thr Ser Lys Asn Gln Val Phe Leu Lys Met Asn Ser Leu Gln Thr Asp
                100                 105                 110

Asp Thr Gly Thr Tyr Tyr Cys Thr Arg Asp Glu Arg Ile Arg Ala Ile
            115                 120                 125
```

Asn Trp Phe Ala Tyr Trp Gly Gln Gly Thr Leu Val Thr Val Ser Ser
130                 135                 140

Ala Lys Thr Thr Pro Lys Leu Val Tyr Pro Leu Ala Pro Gly Gly Gly
145                 150                 155                 160

Gly Ser Gly Gly Gly Ser Gly Gly Gly Ser Tyr Leu Asp Asp
            165                 170                 175

Pro Asn Ser Thr Leu Thr Cys Lys Gly Ser Gln Asn Ile Asp Asn Tyr
            180                 185                 190

Leu Ala Trp Tyr Gln Gln Lys Leu Gly Glu Ala Pro Lys Leu Leu Ile
            195                 200                 205

Tyr Lys Thr Asn Ser Leu Gln Thr Gly Ile Pro Ser Arg Phe Ser Gly
            210                 215                 220

Ser Gly Ser Gly Thr Asp Tyr Thr Leu Thr Ile Ser Ser Leu His Ser
225                 230                 235                 240

Glu Asp Leu Ala Thr Tyr Tyr Cys Tyr Gln Tyr Ile Asn Gly Tyr Thr
                245                 250                 255

Phe Gly Thr Gly Thr Lys Leu Glu Leu Lys Arg Ala Asp Ala Ala Pro
            260                 265                 270

Thr Gly Ser Ile Phe
            275

<210> SEQ ID NO 8
<211> LENGTH: 274
<212> TYPE: PRT
<213> ORGANISM: Artificial Sequence
<220> FEATURE:
<223> OTHER INFORMATION: Synthetic

<400> SEQUENCE: 8

Met Asp Met Arg Ala Pro Ala Gln Ile Phe Gly Phe Leu Leu Leu Leu
1               5                   10                  15

Phe Pro Gly Thr Arg Cys Val Lys Leu Gln Glu Ser Gly Pro Gly Leu
                20                  25                  30

Val Gln Pro Ser Glu Thr Leu Ser Leu Thr Cys Thr Val Ser Gly Phe
            35                  40                  45

Ser Leu Thr Ser Tyr Ser Val Ser Trp Leu Arg Gln Pro Ser Gly Lys
50                  55                  60

Gly Pro Glu Trp Met Gly Arg Met Trp Asp Asp Gly Gly Thr Val Tyr
65                  70                  75                  80

Asn Ser Gly Leu Lys Ser Arg Leu Ser Ile Ser Arg Asp Thr Ser Lys
                85                  90                  95

Asn Gln Val Phe Leu Lys Met Asn Ser Leu Gln Thr Asp Asp Thr Gly
            100                 105                 110

Thr Tyr Tyr Cys Thr Arg Asp Glu Arg Ile Arg Ala Ile Asn Trp Phe
            115                 120                 125

Ala Tyr Trp Gly Gln Gly Thr Leu Val Thr Val Ser Ser Ala Lys Thr
            130                 135                 140

Thr Pro Lys Leu Val Tyr Pro Leu Ala Pro Gly Gly Gly Ser Gly
145                 150                 155                 160

Gly Gly Gly Ser Gly Gly Gly Ser Tyr Leu Asp Asp Pro Asn Ser
                165                 170                 175

Thr Leu Thr Cys Lys Gly Ser Gln Asn Ile Asp Asn Tyr Leu Ala Trp
            180                 185                 190

Tyr Gln Gln Lys Leu Gly Glu Ala Pro Lys Leu Leu Ile Tyr Lys Thr
            195                 200                 205

Asn Ser Leu Gln Thr Gly Ile Pro Ser Arg Phe Ser Gly Ser Gly Ser
            210                 215                 220

Gly Thr Asp Tyr Thr Leu Thr Ile Ser Ser Leu His Ser Glu Asp Leu
225                 230                 235                 240

Ala Thr Tyr Tyr Cys Tyr Gln Tyr Ile Asn Gly Tyr Thr Phe Gly Thr
                245                 250                 255

Gly Thr Lys Leu Glu Leu Lys Arg Ala Asp Ala Ala Pro Thr Gly Ser
            260                 265                 270

Ile Phe

<210> SEQ ID NO 9
<211> LENGTH: 128
<212> TYPE: PRT
<213> ORGANISM: Artificial Sequence
<220> FEATURE:
<223> OTHER INFORMATION: Synthetic

<400> SEQUENCE: 9

Thr Cys Pro Glu Arg Ala Leu Glu Arg Arg Glu Glu Glu Ala Asn Val
1               5                   10                  15

Val Leu Thr Gly Thr Val Glu Gly Ile Leu Asn Val Asp Pro Val Gln
            20                  25                  30

His Thr Tyr Ser Cys Lys Val Arg Val Trp Arg Tyr Leu Lys Gly Lys
        35                  40                  45

Asp Leu Val Ala Arg Glu Ser Leu Leu Asp Gly Gly Asn Lys Val Val
    50                  55                  60

Ile Ser Gly Phe Gly Asp Pro Leu Ile Cys Asp Asn Gln Val Ser Thr
65                  70                  75                  80

Gly Asp Thr Arg Ile Phe Phe Val Asn Pro Ala Pro Tyr Leu Trp
                85                  90                  95

Pro Ala His Lys Asn Glu Leu Met Leu Asn Ser Ser Leu Met Arg Ile
            100                 105                 110

Thr Leu Arg Asn Leu Glu Glu Val Glu Phe Cys Val Glu Asp Lys Pro
        115                 120                 125

<210> SEQ ID NO 10
<211> LENGTH: 453
<212> TYPE: DNA
<213> ORGANISM: Artificial Sequence
<220> FEATURE:
<223> OTHER INFORMATION: Synthetic

<400> SEQUENCE: 10
gactccgaaa gcgattgtac aggctctgaa ccggtcgatg cctttcaggc attcagcgaa      60
ggcaaagaag cgtatgtcct ggttcgtagt acgatccga aagcgcgtga ttgcctcaaa      120
ggggaaccag cggggggaaaa acaggataat accctgccgg taatgatgac ctttaaaaac    180
ggtactgatt gggcatcaac tgactggacg tttacgctgg atggcgcaaa agtgaccgct    240
acattgggga atctgaccca gaatcgtgag gtagtgtacg acagtcaatc gcatcactgt    300
catgtggaca agtcgaaaa agaggttccg gactatgaga tgtggatgct tgatgctggt    360
ggccttgaag tggaggttga atgctgtcgt cagaaactgg aagagttagc ctctggccgt    420
aaccagatgt accctcacct gaaagattgc tga                                  453

<210> SEQ ID NO 11
<211> LENGTH: 150
<212> TYPE: PRT

```
<213> ORGANISM: Artificial Sequence
<220> FEATURE:
<223> OTHER INFORMATION: Synthetic

<400> SEQUENCE: 11

Asp Ser Glu Ser Asp Cys Thr Gly Ser Glu Pro Val Asp Ala Phe Gln
1               5                   10                  15

Ala Phe Ser Glu Gly Lys Glu Ala Tyr Val Leu Val Arg Ser Thr Asp
            20                  25                  30

Pro Lys Ala Arg Asp Cys Leu Lys Gly Glu Pro Ala Gly Glu Lys Gln
        35                  40                  45

Asp Asn Thr Leu Pro Val Met Met Thr Phe Lys Asn Gly Thr Asp Trp
    50                  55                  60

Ala Ser Thr Asp Trp Thr Phe Thr Leu Asp Gly Ala Lys Val Thr Ala
65                  70                  75                  80

Thr Leu Gly Asn Leu Thr Gln Asn Arg Glu Val Val Tyr Asp Ser Gln
                85                  90                  95

Ser His His Cys His Val Asp Lys Val Glu Lys Glu Val Pro Asp Tyr
            100                 105                 110

Glu Met Trp Met Leu Asp Ala Gly Gly Leu Glu Val Glu Val Glu Cys
            115                 120                 125

Cys Arg Gln Lys Leu Glu Glu Leu Ala Ser Gly Arg Asn Gln Met Tyr
        130                 135                 140

Pro His Leu Lys Asp Cys
145                 150

<210> SEQ ID NO 12
<211> LENGTH: 255
<212> TYPE: PRT
<213> ORGANISM: Artificial Sequence
<220> FEATURE:
<223> OTHER INFORMATION: Synthetic

<400> SEQUENCE: 12

Val Asp Gly Asp Cys Gly Pro Pro Asp Ile Pro Asn Ala Arg Pro
1               5                   10                  15

Ile Leu Gly Arg His Ser Lys Phe Ala Glu Gln Ser Lys Val Ala Tyr
            20                  25                  30

Ser Cys Asn Asn Gly Phe Lys Gln Val Pro Asp Lys Ser Asn Ile Val
        35                  40                  45

Val Cys Leu Glu Asn Gly Gln Trp Ser Ser His Glu Thr Phe Cys Glu
    50                  55                  60

Lys Ser Cys Val Ala Pro Glu Arg Leu Ser Phe Ala Ser Leu Lys Lys
65                  70                  75                  80

Glu Tyr Leu Asn Met Asn Phe Phe Pro Val Gly Thr Ile Val Glu Tyr
                85                  90                  95

Glu Cys Arg Pro Gly Phe Arg Lys Gln Pro Pro Leu Pro Gly Lys Ala
            100                 105                 110

Thr Cys Leu Glu Asp Leu Val Trp Ser Pro Val Ala Gln Phe Cys Lys
            115                 120                 125

Lys Lys Ser Cys Pro Asn Pro Lys Asp Leu Asp Asn Gly His Ile Asn
        130                 135                 140

Ile Pro Thr Gly Ile Leu Phe Gly Ser Glu Ile Asn Phe Ser Cys Asn
145                 150                 155                 160

Pro Gly Tyr Arg Leu Val Gly Val Ser Ser Thr Phe Cys Ser Val Thr
                165                 170                 175
```

-continued

Gly Asn Thr Val Asp Trp Asp Asp Glu Phe Pro Val Cys Thr Glu Ile
            180                 185                 190

His Cys Pro Glu Pro Pro Lys Ile Asn Asn Gly Ile Met Arg Gly Glu
        195                 200                 205

Ser Asp Ser Tyr Thr Tyr Ser Gln Val Val Thr Tyr Ser Cys Asp Lys
    210                 215                 220

Gly Phe Ile Leu Val Gly Asn Ala Ser Ile Tyr Cys Thr Val Ser Lys
225                 230                 235                 240

Ser Asp Val Gly Gln Trp Ser Ser Pro Pro Arg Cys Ile Glu
            245                 250                 255

<210> SEQ ID NO 13
<211> LENGTH: 540
<212> TYPE: DNA
<213> ORGANISM: Artificial Sequence
<220> FEATURE:
<223> OTHER INFORMATION: Synthetic

<400> SEQUENCE: 13
gctagcgaac agcagaccgc agaccaactc ctagcccgag ctgatgctgc caaggccctc        60
gctgaaggca gcggcagcgc ggactccgaa agcgattgta caggctctga accggtcgat       120
gcctttcagg cattcagcga aggcaaagaa gcgtatgtcc tggttcgtag tacggatccg       180
aaagcgcgtg attgcctcaa aggggaacca gcggggggaaa acaggataa taccctgccg       240 gtaatgatga cctttaaaaa cggtactgat tgggcatcaa ctgactggac gtttacgctg       300
gatggcgcaa aagtgaccgc tacattgggg aatctgaccc agaatcgtga ggtagtgtac       360
gacagtcaat cgcatcactg tcatgtggac aaagtcgaaa aagaggttcc ggactatgag       420
atgtggatgc ttgatgctgg tggccttgaa gtggaggttg aatgctgtcg tcagaaactg       480
gaagagttag cctctggccg taaccagatg taccctcacc tgaaagattg ctgagaattc       540

<210> SEQ ID NO 14
<211> LENGTH: 198
<212> TYPE: PRT
<213> ORGANISM: Artificial Sequence
<220> FEATURE:
<223> OTHER INFORMATION: Synthetic

<400> SEQUENCE: 14

Met Gly Ser Ser His His His His His His Ser Ser Gly Leu Val Pro
1               5                   10                  15

Arg Gly Ser His Met Ala Ser Glu Gln Gln Thr Ala Asp Gln Leu Leu
            20                  25                  30

Ala Arg Ala Asp Ala Ala Lys Ala Leu Ala Glu Gly Ser Gly Ser Ala
        35                  40                  45

Asp Ser Glu Ser Asp Cys Thr Gly Ser Glu Pro Val Asp Ala Phe Gln
    50                  55                  60

Ala Phe Ser Glu Gly Lys Glu Ala Tyr Val Leu Val Arg Ser Thr Asp
65                  70                  75                  80

Pro Lys Ala Arg Asp Cys Leu Lys Gly Glu Pro Ala Gly Glu Lys Gln
            85                  90                  95

Asp Asn Thr Leu Pro Val Met Met Thr Phe Lys Asn Gly Thr Asp Trp
            100                 105                 110

Ala Ser Thr Asp Trp Thr Phe Thr Leu Asp Gly Ala Lys Val Thr Ala
        115                 120                 125

Thr Leu Gly Asn Leu Thr Gln Asn Arg Glu Val Val Tyr Asp Ser Gln
    130                 135                 140

```
Ser His His Cys His Val Asp Lys Val Glu Lys Glu Val Pro Asp Tyr
145                 150                 155                 160

Glu Met Trp Met Leu Asp Ala Gly Gly Leu Glu Val Glu Val Glu Cys
                165                 170                 175

Cys Arg Gln Lys Leu Glu Glu Leu Ala Ser Gly Arg Asn Gln Met Tyr
            180                 185                 190

Pro His Leu Lys Asp Cys
        195

<210> SEQ ID NO 15
<211> LENGTH: 513
<212> TYPE: DNA
<213> ORGANISM: Artificial Sequence
<220> FEATURE:
<223> OTHER INFORMATION: Synthetic

<400> SEQUENCE: 15
gctagcttta acattagcac cagcattcgc ggcaaagtgg gcagcggcag cgcggactcc      60
gaaagcgatt gtacaggctc tgaaccggtc gatgcctttc aggcattcag cgaaggcaaa     120
gaagcgtatg tcctggttcg tagtacggat ccgaaagcgc gtgattgcct caaaggggaa     180
ccagcggggg aaaaacagga taatacccctg ccggtaatga tgacctttaa aaacggtact     240
gattgggcat caactgactg gacgtttacg ctggatggcg caaaagtgac cgctacattg     300
gggaatctga cccagaatcg tgaggtagtg tacgacagtc aatcgcatca ctgtcatgtg     360
gacaaagtcg aaaagaggt tccggactat gagatgtgga tgcttgatgc tggtggcctt     420
gaagtggagg ttgaatgctg tcgtcagaaa ctggaagagt tagcctctgg ccgtaaccag     480
atgtaccctc acctgaaaga ttgctgagaa ttc                                   513

<210> SEQ ID NO 16
<211> LENGTH: 170
<212> TYPE: PRT
<213> ORGANISM: Artificial Sequence
<220> FEATURE:
<223> OTHER INFORMATION: Synthetic

<400> SEQUENCE: 16

Ala Ser Phe Asn Ile Ser Thr Ser Ile Arg Gly Lys Val Gly Ser Gly
1               5                   10                  15

Ser Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
```

```
                145                 150                 155                 160
Met Tyr Pro His Leu Lys Asp Cys Glu Phe
                165                 170

<210> SEQ ID NO 17
<211> LENGTH: 513
<212> TYPE: DNA
<213> ORGANISM: Artificial Sequence
<220> FEATURE:
<223> OTHER INFORMATION: Synthetic

<400> SEQUENCE: 17
gctagctgcg atattttac  caacagccgc ggcaaacgcg gcagcggcag cgcggactcc     60
gaaagcgatt gtacaggctc tgaaccggtc gatgcctttc aggcattcag cgaaggcaaa    120
gaagcgtatg tcctggttcg tagtacggat ccgaaagcgc gtgattgcct caaaggggaa    180
ccagcggggg aaaaacagga taatacccctg ccggtaatga tgaccttaa  aaacggtact    240 gattgggcat caactgactg gacgtttacg ctggatggcg caaaagtgac cgctacattg    300
gggaatctga cccagaatcg tgaggtagtg tacgacagtc aatcgcatca ctgtcatgtg    360
gacaaagtcg aaaagaggt tccggactat gagatgtgga tgcttgatgc tggtggcctt    420
gaagtggagg ttgaatgctg tcgtcagaaa ctggaagagt tagcctctgg ccgtaaccag    480
atgtaccctc acctgaaaga ttgctgagaa ttc                                 513

<210> SEQ ID NO 18
<211> LENGTH: 170
<212> TYPE: PRT
<213> ORGANISM: Artificial Sequence
<220> FEATURE:
<223> OTHER INFORMATION: Synthetic

<400> SEQUENCE: 18

Ala Ser Cys Asp Ile Phe Thr Asn Ser Arg Gly Lys Arg Gly Ser Gly
1               5                   10                  15

Ser Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160

Met Tyr Pro His Leu Lys Asp Cys Glu Phe
                165                 170

<210> SEQ ID NO 19
<211> LENGTH: 18
```

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
ggtagcggca gcggtagc                                            18

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
ggtagcggca gcggtagcgg tagcggcagc                               30

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
ggtgaaaatt tgtatttca atctggtggt                                30

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
tccgcttgtt actgtgagct ttcc                                     24

<210> SEQ ID NO 23
<211> LENGTH: 51
<212> TYPE: DNA
<213> ORGANISM: Artificial Sequence
<220> FEATURE:
<223> OTHER INFORMATION: Synthetic

<400> SEQUENCE: 23
cgaccagcct gtaagattcc aaatgacctg aagcagaaag ttatgaatca c        51

<210> SEQ ID NO 24
<211> LENGTH: 45
<212> TYPE: DNA
<213> ORGANISM: Artificial Sequence
<220> FEATURE:
<223> OTHER INFORMATION: Synthetic

<400> SEQUENCE: 24
ggtggaggag gttctggagg cggtggaagt ggtggcggag gtagc               45

<210> SEQ ID NO 25
<211> LENGTH: 12
<212> TYPE: DNA
<213> ORGANISM: Artificial Sequence
<220> FEATURE:
<223> OTHER INFORMATION: Synthetic

<400> SEQUENCE: 25

```
ggtggttctg gt                                                           12

<210> SEQ ID NO 26
<211> LENGTH: 24
<212> TYPE: DNA
<213> ORGANISM: Artificial Sequence
<220> FEATURE:
<223> OTHER INFORMATION: Synthetic

<400> SEQUENCE: 26
ggtggttctg gtggtggttc tggt                                              24

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
ggtggttctg gtggtggttc tggtggtggt tctggt                                 36

<210> SEQ ID NO 28
<211> LENGTH: 108
<212> TYPE: DNA
<213> ORGANISM: Artificial Sequence
<220> FEATURE:
<223> OTHER INFORMATION: Synthetic

<400> SEQUENCE: 28
ggtggttctg ccggtggctc cggttctggc tccagcggtg gcagctctgg tgcgtccggc       60
acgggtactg cgggtggcac tggcagcggt tccggtactg gctctggc                   108

<210> SEQ ID NO 29
<211> LENGTH: 108
<212> TYPE: DNA
<213> ORGANISM: Artificial Sequence
<220> FEATURE:
<223> OTHER INFORMATION: Synthetic

<400> SEQUENCE: 29
ggtggttctg gcggcggttc tgaaggtggc ggctccgaag gcggcggcag cgagggcggt       60
ggtagcgaag gtggtggctc cgagggtggc ggttccggcg gcggtagc                   108

<210> SEQ ID NO 30
<211> LENGTH: 192
<212> TYPE: DNA
<213> ORGANISM: Artificial Sequence
<220> FEATURE:
<223> OTHER INFORMATION: Synthetic

<400> SEQUENCE: 30
gtggataaca aatttaacaa agaaatgtgg gcggcgtggg aagaaattcg taacctgccg       60
aacctgaacg gctggcagat gaccgcgttt attgcgagcc tggtggatga tccgagccag      120
agcgcgaacc tgctggcgga agcgaaaaaa ctgaacgatg cgcaggcgcc gaaaaccggc      180
ggtggttctg gt                                                          192

<210> SEQ ID NO 31
<211> LENGTH: 204
<212> TYPE: DNA
<213> ORGANISM: Artificial Sequence
<220> FEATURE:
<223> OTHER INFORMATION: Synthetic
```

<400> SEQUENCE: 31

| | | |
|---|---|---|
| gtggataaca aatttaacaa agaaatgtgg gcggcgtggg aagaaattcg taacctgccg | 60 |
| aacctgaacg gctggcagat gaccgcgttt attgcgagcc tggtggatga tccgagccag | 120 |
| agcgcgaacc tgctggcgga agcgaaaaaa ctgaacgatg cgcaggcgcc gaaaaccggc | 180 |
| ggtggttctg gtggtggttc tggt | 204 |

<210> SEQ ID NO 32
<211> LENGTH: 216
<212> TYPE: DNA
<213> ORGANISM: Artificial Sequence
<220> FEATURE:
<223> OTHER INFORMATION: Synthetic

<400> SEQUENCE: 32

| | | |
|---|---|---|
| gtggataaca aatttaacaa agaaatgtgg gcggcgtggg aagaaattcg taacctgccg | 60 |
| aacctgaacg gctggcagat gaccgcgttt attgcgagcc tggtggatga tccgagccag | 120 |
| agcgcgaacc tgctggcgga agcgaaaaaa ctgaacgatg cgcaggcgcc gaaaaccggc | 180 |
| ggtggttctg gtggtggttc tggtggtggt tctggt | 216 |

<210> SEQ ID NO 33
<211> LENGTH: 45
<212> TYPE: DNA
<213> ORGANISM: Artificial Sequence
<220> FEATURE:
<223> OTHER INFORMATION: Synthetic

<400> SEQUENCE: 33
ggtggaggag gctctggtgg aggcggtagc ggaggcggag ggtcg     45

<210> SEQ ID NO 34
<211> LENGTH: 532
<212> TYPE: PRT
<213> ORGANISM: Artificial Sequence
<220> FEATURE:
<223> OTHER INFORMATION: Synthetic

<400> SEQUENCE: 34

```
Met Arg Ala Gln Arg Gly Leu Ile Leu Leu Leu Leu Leu Ala Val
1               5                  10                  15

Phe Cys Ser Thr Ala Val Ser Leu Thr Val Lys Leu Gln Glu Ser Gly
            20                  25                  30

Pro Gly Leu Val Gln Pro Ser Glu Thr Leu Ser Leu Thr Cys Thr Val
        35                  40                  45

Ser Gly Phe Ser Leu Thr Ser Tyr Ser Val Ser Trp Leu Arg Gln Pro
    50                  55                  60

Ser Gly Lys Gly Pro Glu Trp Met Gly Arg Met Trp Asp Asp Gly
65                  70                  75                  80

Thr Val Tyr Asn Ser Gly Leu Lys Ser Arg Leu Ser Ile Ser Arg Asp
                85                  90                  95

Thr Ser Lys Asn Gln Val Phe Leu Lys Met Asn Ser Leu Gln Thr Asp
            100                 105                 110

Asp Thr Gly Thr Tyr Tyr Cys Thr Arg Asp Glu Arg Ile Arg Ala Ile
        115                 120                 125

Asn Trp Phe Ala Tyr Trp Gly Gln Gly Thr Leu Val Thr Val Ser Ser
    130                 135                 140

Ala Lys Thr Thr Pro Lys Leu Val Tyr Pro Leu Ala Pro Gly Gly Gly
```

```
                145                 150                 155                 160
        Gly Ser Gly Gly Gly Ser Gly Gly Gly Ser Tyr Leu Asp Asp
                        165                 170                 175
        Pro Asn Ser Thr Leu Thr Cys Lys Gly Ser Gln Asn Ile Asp Asn Tyr
                        180                 185                 190
        Leu Ala Trp Tyr Gln Gln Lys Leu Gly Glu Ala Pro Lys Leu Leu Ile
                        195                 200                 205
        Tyr Lys Thr Asn Ser Leu Gln Thr Gly Ile Pro Ser Arg Phe Ser Gly
                        210                 215                 220
        Ser Gly Ser Gly Thr Asp Tyr Thr Leu Thr Ile Ser Ser Leu His Ser
        225                 230                 235                 240
        Glu Asp Leu Ala Thr Tyr Tyr Cys Tyr Gln Tyr Ile Asn Gly Tyr Thr
                        245                 250                 255
        Phe Gly Thr Gly Thr Lys Leu Glu Leu Lys Arg Ala Asp Ala Ala Pro
                        260                 265                 270
        Thr Gly Ser Ile Phe Val Asp Gly Asp Cys Gly Pro Pro Asp Ile
                        275                 280                 285
        Pro Asn Ala Arg Pro Ile Leu Gly Arg His Ser Lys Phe Ala Glu Gln
                        290                 295                 300
        Ser Lys Val Ala Tyr Ser Cys Asn Asn Gly Phe Lys Gln Val Pro Asp
        305                 310                 315                 320
        Lys Ser Asn Ile Val Cys Leu Glu Asn Gly Gln Trp Ser Ser His
                        325                 330                 335
        Glu Thr Phe Cys Glu Lys Ser Cys Val Ala Pro Glu Arg Leu Ser Phe
                        340                 345                 350
        Ala Ser Leu Lys Lys Glu Tyr Leu Asn Met Asn Phe Phe Pro Val Gly
                        355                 360                 365
        Thr Ile Val Glu Tyr Glu Cys Arg Pro Gly Phe Arg Lys Gln Pro Pro
                        370                 375                 380
        Leu Pro Gly Lys Ala Thr Cys Leu Glu Asp Leu Val Trp Ser Pro Val
        385                 390                 395                 400
        Ala Gln Phe Cys Lys Lys Lys Ser Cys Pro Asn Pro Lys Asp Leu Asp
                        405                 410                 415
        Asn Gly His Ile Asn Ile Pro Thr Gly Ile Leu Phe Gly Ser Glu Ile
                        420                 425                 430
        Asn Phe Ser Cys Asn Pro Gly Tyr Arg Leu Val Gly Val Ser Ser Thr
                        435                 440                 445
        Phe Cys Ser Val Thr Gly Asn Thr Val Asp Trp Asp Asp Glu Phe Pro
        450                 455                 460
        Val Cys Thr Glu Ile His Cys Pro Glu Pro Pro Lys Ile Asn Asn Gly
        465                 470                 475                 480
        Ile Met Arg Gly Glu Ser Asp Ser Tyr Thr Tyr Ser Gln Val Val Thr
                        485                 490                 495
        Tyr Ser Cys Asp Lys Gly Phe Ile Leu Val Gly Asn Ala Ser Ile Tyr
                        500                 505                 510
        Cys Thr Val Ser Lys Ser Asp Val Gly Gln Trp Ser Ser Pro Pro Pro
                        515                 520                 525
        Arg Cys Ile Glu
            530

<210> SEQ ID NO 35
<211> LENGTH: 529
<212> TYPE: PRT
<213> ORGANISM: Artificial Sequence
```

<220> FEATURE:
<223> OTHER INFORMATION: Synthetic

<400> SEQUENCE: 35

Met Asp Met Arg Ala Pro Ala Gln Ile Phe Gly Phe Leu Leu Leu Leu
1               5                   10                  15

Phe Pro Gly Thr Arg Cys Val Lys Leu Gln Glu Ser Gly Pro Gly Leu
            20                  25                  30

Val Gln Pro Ser Glu Thr Leu Ser Leu Thr Cys Thr Val Ser Gly Phe
        35                  40                  45

Ser Leu Thr Ser Tyr Ser Val Ser Trp Leu Arg Gln Pro Ser Gly Lys
    50                  55                  60

Gly Pro Glu Trp Met Gly Arg Met Trp Asp Asp Gly Thr Val Tyr
65                  70                  75                  80

Asn Ser Gly Leu Lys Ser Arg Leu Ser Ile Ser Arg Asp Thr Ser Lys
                85                  90                  95

Asn Gln Val Phe Leu Lys Met Asn Ser Leu Gln Thr Asp Asp Thr Gly
            100                 105                 110

Thr Tyr Tyr Cys Thr Arg Asp Glu Arg Ile Arg Ala Ile Asn Trp Phe
        115                 120                 125

Ala Tyr Trp Gly Gln Gly Thr Leu Val Thr Val Ser Ser Ala Lys Thr
    130                 135                 140

Thr Pro Lys Leu Val Tyr Pro Leu Ala Pro Gly Gly Gly Ser Gly
145                 150                 155                 160

Gly Gly Gly Ser Gly Gly Gly Ser Tyr Leu Asp Asp Pro Asn Ser
                165                 170                 175

Thr Leu Thr Cys Lys Gly Ser Gln Asn Ile Asp Asn Tyr Leu Ala Trp
        180                 185                 190

Tyr Gln Gln Lys Leu Gly Glu Ala Pro Lys Leu Leu Ile Tyr Lys Thr
    195                 200                 205

Asn Ser Leu Gln Thr Gly Ile Pro Ser Arg Phe Ser Gly Ser Gly Ser
    210                 215                 220

Gly Thr Asp Tyr Thr Leu Thr Ile Ser Ser Leu His Ser Glu Asp Leu
225                 230                 235                 240

Ala Thr Tyr Tyr Cys Tyr Gln Tyr Ile Asn Gly Tyr Thr Phe Gly Thr
                245                 250                 255

Gly Thr Lys Leu Glu Leu Lys Arg Ala Asp Ala Ala Pro Thr Gly Ser
            260                 265                 270

Ile Phe Val Asp Gly Asp Cys Gly Pro Pro Asp Ile Pro Asn Ala
        275                 280                 285

Arg Pro Ile Leu Gly Arg His Ser Lys Phe Ala Glu Gln Ser Lys Val
    290                 295                 300

Ala Tyr Ser Cys Asn Asn Gly Phe Lys Gln Val Pro Asp Lys Ser Asn
305                 310                 315                 320

Ile Val Val Cys Leu Glu Asn Gly Gln Trp Ser Ser His Glu Thr Phe
                325                 330                 335

Cys Glu Lys Ser Cys Val Ala Pro Glu Arg Leu Ser Phe Ala Ser Leu
            340                 345                 350

Lys Lys Glu Tyr Leu Asn Met Asn Phe Phe Pro Val Gly Thr Ile Val
        355                 360                 365

Glu Tyr Glu Cys Arg Pro Gly Phe Arg Lys Gln Pro Pro Leu Pro Gly
    370                 375                 380

Lys Ala Thr Cys Leu Glu Asp Leu Val Trp Ser Pro Val Ala Gln Phe
385                 390                 395                 400

```
Cys Lys Lys Lys Ser Cys Pro Asn Pro Lys Asp Leu Asp Asn Gly His
                405                 410                 415

Ile Asn Ile Pro Thr Gly Ile Leu Phe Gly Ser Glu Ile Asn Phe Ser
                420                 425                 430

Cys Asn Pro Gly Tyr Arg Leu Val Gly Val Ser Ser Thr Phe Cys Ser
                435                 440                 445

Val Thr Gly Asn Thr Val Asp Trp Asp Asp Glu Phe Pro Val Cys Thr
        450                 455                 460

Glu Ile His Cys Pro Glu Pro Pro Lys Ile Asn Asn Gly Ile Met Arg
465                 470                 475                 480

Gly Glu Ser Asp Ser Tyr Thr Tyr Ser Gln Val Val Thr Tyr Ser Cys
                485                 490                 495

Asp Lys Gly Phe Ile Leu Val Gly Asn Ala Ser Ile Tyr Cys Thr Val
                500                 505                 510

Ser Lys Ser Asp Val Gly Gln Trp Ser Ser Pro Pro Pro Arg Cys Ile
        515                 520                 525

Glu

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Cys Glu Gly Pro Phe Gly Pro Arg His Asp Leu Thr Phe Cys Trp
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)

<400> SEQUENCE: 37

Ser His Leu Gly Leu Ala Arg
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)

<400> SEQUENCE: 38

Arg Leu Leu Leu Ala Arg
1               5
```